United States Patent
Moseley et al.

(10) Patent No.: US 9,180,224 B2
(45) Date of Patent: *Nov. 10, 2015

(54) COMPOSITE BONE GRAFT SUBSTITUTE CEMENT AND ARTICLES PRODUCED THEREFROM

(75) Inventors: Jon P. Moseley, Arlington, TN (US); Michael E. Carroll, Memphis, TN (US); Jonathan D. McCanless, Memphis, TN (US)

(73) Assignee: Agnovos Healthcare, LLC, Webster, NY (US)

( * ) Notice: Subject to any disclaimer, the term of this patent is extended or adjusted under 35 U.S.C. 154(b) by 305 days.

This patent is subject to a terminal disclaimer.

(21) Appl. No.: 12/814,033

(22) Filed: Jun. 11, 2010

(65) Prior Publication Data

US 2010/0249794 A1 Sep. 30, 2010

Related U.S. Application Data

(63) Continuation of application No. 11/530,085, filed on Sep. 8, 2006, now Pat. No. 7,754,246.

(60) Provisional application No. 60/715,542, filed on Sep. 9, 2005.

(51) Int. Cl.
*A61L 27/02* (2006.01)
*A61L 27/12* (2006.01)
*A61L 27/36* (2006.01)
*A61L 27/42* (2006.01)
*A61L 27/58* (2006.01)

(52) U.S. Cl.
CPC .............. *A61L 27/427* (2013.01); *A61L 27/025* (2013.01); *A61L 27/12* (2013.01); *A61L 27/365* (2013.01); *A61L 27/58* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | |
|---|---|---|
| 2,043,238 A | 6/1936 | Curtis |
| 2,616,789 A | 3/1951 | Hoggatt |
| 3,090,094 A | 5/1963 | Schwartzwalder et al. |
| 3,573,947 A | 4/1971 | Kinkade et al. |
| 3,616,841 A | 11/1971 | Walz |
| 3,662,405 A | 5/1972 | Bortz et al. |
| 3,787,900 A | 1/1974 | McGee |
| 3,790,365 A | 2/1974 | Niebylski et al. |
| 3,813,312 A | 5/1974 | Kinkade et al. |
| 3,816,952 A | 6/1974 | Niebyski et al. |
| 3,829,326 A | 8/1974 | Soejima et al. |
| 3,899,556 A | 8/1975 | Heide et al. |
| 3,905,047 A | 9/1975 | Long |
| 4,000,525 A | 1/1977 | Klawitter et al. |
| 4,076,888 A | 2/1978 | Perugini et al. |
| 4,097,935 A | 7/1978 | Jarcho |
| 4,149,893 A | 4/1979 | Aoki et al. |
| 4,158,684 A | 6/1979 | Klawitter et al. |
| 4,168,326 A | 9/1979 | Broemer et al. |
| 4,222,128 A | 9/1980 | Tomonaga et al. |
| 4,224,072 A | 9/1980 | Stewart |
| 4,237,559 A | 12/1980 | Borom |
| 4,349,518 A | 9/1982 | Long et al. |
| 4,365,356 A | 12/1982 | Broemer et al. |
| 4,371,484 A | 2/1983 | Inukai et al. |
| 4,376,168 A | 3/1983 | Takami et al. |
| 4,430,760 A | 2/1984 | Smestad |
| 4,447,548 A | 5/1984 | Huebsch, III |
| 4,517,069 A | 5/1985 | Harney et al. |
| 4,568,536 A | 2/1986 | Kronenthal et al. |
| 4,569,920 A | 2/1986 | Smith-Johannsen |
| 4,595,713 A | 6/1986 | St. John |
| 4,599,085 A | 7/1986 | Riess et al. |
| 4,602,953 A | 7/1986 | Wiech, Jr. |
| 4,612,009 A | 9/1986 | Drobnik et al. |
| 4,612,053 A | 9/1986 | Brown et al. |

(Continued)

FOREIGN PATENT DOCUMENTS

| | | |
|---|---|---|
| EP | 0 263 489 A1 | 4/1988 |
| EP | 0 335 359 A2 | 10/1989 |
| EP | 0 543 765 A1 | 5/1993 |
| EP | 0 987 032 B1 | 3/2000 |
| EP | 1 301 219 B1 | 4/2003 |
| EP | 1 601 387 B1 | 12/2005 |
| JP | 10 151188 A | 6/1998 |

(Continued)

OTHER PUBLICATIONS

Burstein et al., Contribution of Collagen and Mineral to the Elastic-Plastic Properties of Bone,The Journal of Bone and Joint Surgery (1975), vol. 67-A, No. 7, pp. 956-961.*

(Continued)

*Primary Examiner* — Abigail Fisher
*Assistant Examiner* — Frank Choi
(74) *Attorney, Agent, or Firm* — Wolf, Greenfield & Sacks, P.C.

(57) ABSTRACT

The invention provides a particulate composition adapted for forming a bone graft substitute cement upon mixing with an aqueous solution, including i) a calcium sulfate hemihydrate powder having a bimodal particle distribution and a median particle size of about 5 to about 20 microns, wherein the calcium sulfate hemihydrate is present at a concentration of at least about 70 weight percent based on the total weight of the particulate composition; ii) a monocalcium phosphate monohydrate powder; and iii) a β-tricalcium phosphate powder having a median particle size of less than about 20 microns. Bone graft substitute cements made therefrom, a bone graft substitute kit comprising the particulate composition, methods of making and using the particulate composition, and articles made from the bone graft substitute cement are also provided.

77 Claims, 5 Drawing Sheets

(56) References Cited

U.S. PATENT DOCUMENTS

| | | |
|---|---|---|
| 4,619,655 A | 10/1986 | Hanker et al. |
| 4,626,392 A | 12/1986 | Kondo et al. |
| 4,629,464 A | 12/1986 | Takata et al. |
| 4,650,665 A | 3/1987 | Kronenthal et al. |
| 4,654,314 A | 3/1987 | Takagi et al. |
| 4,659,617 A | 4/1987 | Fujii et al. |
| 4,673,355 A | 6/1987 | Farris et al. |
| 4,681,763 A | 7/1987 | Nathanson et al. |
| 4,693,748 A | 9/1987 | Kobayashi et al. |
| 4,693,986 A | 9/1987 | Vit et al. |
| 4,777,153 A | 10/1988 | Sonuparlak et al. |
| 4,794,046 A | 12/1988 | Nagai |
| 4,810,685 A | 3/1989 | Twigg et al. |
| 4,820,306 A | 4/1989 | Gorman et al. |
| 4,836,994 A | 6/1989 | Inoue et al. |
| 4,838,922 A | 6/1989 | Green |
| 4,843,112 A | 6/1989 | Gerhart et al. |
| 4,861,733 A | 8/1989 | White |
| 4,880,660 A | 11/1989 | Aasen et al. |
| 4,882,149 A | 11/1989 | Spector |
| 4,892,734 A | 1/1990 | Leonard |
| 4,950,294 A | 8/1990 | Hakamatsuka |
| 4,957,509 A | 9/1990 | Tamari et al. |
| 4,959,104 A | 9/1990 | Iino et al. |
| 4,960,426 A | 10/1990 | Atsumi |
| 4,967,509 A | 11/1990 | Storey et al. |
| 4,969,913 A | 11/1990 | Ojima |
| 4,975,526 A | 12/1990 | Kuberasampath et al. |
| 4,990,163 A | 2/1991 | Ducheyne et al. |
| 4,994,030 A | 2/1991 | Glowczewskie et al. |
| 5,015,610 A | 5/1991 | Dwivedi |
| 5,017,518 A | 5/1991 | Hirayama et al. |
| 5,030,396 A | 7/1991 | Saita et al. |
| 5,061,286 A | 10/1991 | Lyle |
| 5,061,660 A | 10/1991 | Park et al. |
| 5,071,434 A | 12/1991 | Tsuzuki et al. |
| 5,073,357 A | 12/1991 | Takagi et al. |
| 5,073,373 A | 12/1991 | O'Leary et al. |
| 5,137,534 A | 8/1992 | Sumita |
| 5,141,510 A | 8/1992 | Takagi et al. |
| 5,147,403 A | 9/1992 | Gitelis |
| 5,149,368 A | 9/1992 | Liu et al. |
| 5,152,791 A | 10/1992 | Hakamatsuka et al. |
| 5,158,726 A | 10/1992 | Saita et al. |
| 5,162,114 A | 11/1992 | Kuberasampath et al. |
| 5,171,326 A | 12/1992 | Ducheyne et al. |
| 5,171,720 A | 12/1992 | Kawakami |
| 5,178,845 A | 1/1993 | Constantz et al. |
| 5,180,426 A | 1/1993 | Sumita |
| 5,192,325 A | 3/1993 | Kijima et al. |
| 5,211,664 A | 5/1993 | Tepic et al. |
| 5,218,035 A | 6/1993 | Liu |
| 5,219,897 A | 6/1993 | Murray |
| 5,236,456 A | 8/1993 | O'Leary et al. |
| 5,236,971 A | 8/1993 | Murray |
| 5,262,166 A | 11/1993 | Liu et al. |
| 5,264,214 A | 11/1993 | Rhee et al. |
| 5,281,251 A | 1/1994 | Kenny et al. |
| 5,281,265 A | 1/1994 | Liu |
| 5,282,861 A | 2/1994 | Kaplan |
| 5,284,655 A | 2/1994 | Bogdansky et al. |
| 5,284,695 A | 2/1994 | Barlow et al. |
| 5,290,558 A | 3/1994 | O'Leary et al. |
| 5,296,180 A | 3/1994 | Hayes et al. |
| 5,298,254 A | 3/1994 | Prewett et al. |
| 5,306,304 A | 4/1994 | Gendler |
| 5,306,673 A | 4/1994 | Hermansson et al. |
| 5,314,476 A | 5/1994 | Prewett et al. |
| 5,314,478 A | 5/1994 | Oka et al. |
| 5,320,844 A | 6/1994 | Liu |
| 5,336,699 A | 8/1994 | Cooke et al. |
| 5,338,356 A | 8/1994 | Hirano et al. |
| 5,356,629 A | 10/1994 | Sander et al. |
| 5,366,507 A | 11/1994 | Sottosanti |
| 5,385,887 A | 1/1995 | Yim et al. |
| 5,397,362 A | 3/1995 | Noda |
| 5,397,759 A | 3/1995 | Torobin |
| 5,405,390 A | 4/1995 | O'Leary et al. |
| 5,417,975 A | 5/1995 | Lussi et al. |
| 5,425,769 A | 6/1995 | Snyders, Jr. |
| 5,427,754 A | 6/1995 | Nagata et al. |
| 5,439,684 A | 8/1995 | Prewett et al. |
| 5,462,722 A | 10/1995 | Liu et al. |
| 5,482,551 A | 1/1996 | Morris et al. |
| 5,484,601 A | 1/1996 | O'Leary et al. |
| 5,503,164 A | 4/1996 | Friedman |
| 5,507,813 A | 4/1996 | Dowd et al. |
| 5,510,396 A | 4/1996 | Prewett et al. |
| 5,512,610 A | 4/1996 | Lin |
| 5,531,791 A | 7/1996 | Wolfinbarger, Jr. |
| 5,531,794 A | 7/1996 | Takagi et al. |
| 5,543,209 A | 8/1996 | Duquet et al. |
| 5,569,308 A | 10/1996 | Sottosanti |
| 5,573,771 A | 11/1996 | Geistlich et al. |
| 5,578,662 A | 11/1996 | Bennett et al. |
| 5,605,713 A | 2/1997 | Boltong |
| 5,614,206 A | 3/1997 | Randolph et al. |
| 5,618,549 A | 4/1997 | Patat et al. |
| 5,624,674 A | 4/1997 | Seare, Jr. |
| 5,639,402 A | 6/1997 | Barlow et al. |
| 5,676,146 A | 10/1997 | Scarborough |
| 5,676,699 A | 10/1997 | Gogolewski et al. |
| 5,676,976 A | 10/1997 | Lee et al. |
| 5,681,572 A | 10/1997 | Seare, Jr. |
| 5,681,873 A | 10/1997 | Norton et al. |
| 5,683,496 A | 11/1997 | Ison et al. |
| 5,697,981 A | 12/1997 | Ison et al. |
| 5,700,289 A | 12/1997 | Breitbart et al. |
| 5,702,449 A | 12/1997 | McKay |
| 5,707,962 A | 1/1998 | Chen et al. |
| 5,714,103 A | 2/1998 | Bauer et al. |
| 5,717,006 A | 2/1998 | Daculsi et al. |
| 5,727,945 A | 3/1998 | Dannenbaum |
| 5,746,822 A | 5/1998 | Espinoza et al. |
| 5,756,127 A | 5/1998 | Grisoni et al. |
| 5,763,416 A | 6/1998 | Bonadio et al. |
| 5,766,618 A | 6/1998 | Laurencin et al. |
| 5,769,897 A | 6/1998 | Härle |
| 5,776,233 A | 7/1998 | Wiedemann et al. |
| 5,782,971 A | 7/1998 | Constantz et al. |
| 5,788,976 A | 8/1998 | Bradford |
| 5,807,567 A | 9/1998 | Randolph et al. |
| 5,820,632 A | 10/1998 | Constantz et al. |
| 5,824,087 A | 10/1998 | Aspden et al. |
| 5,830,493 A | 11/1998 | Yokota et al. |
| 5,833,959 A | 11/1998 | Atsumi et al. |
| 5,846,312 A | 12/1998 | Ison et al. |
| 5,861,445 A | 1/1999 | Xu et al. |
| 5,899,939 A | 5/1999 | Boyce et al. |
| 5,910,315 A | 6/1999 | Stevenson et al. |
| 5,914,133 A | 6/1999 | Tsujino |
| 5,925,444 A | 7/1999 | Katsumura et al. |
| 5,948,426 A | 9/1999 | Jefferies |
| 5,948,428 A | 9/1999 | Lee et al. |
| 5,964,805 A | 10/1999 | Stone |
| 5,972,368 A | 10/1999 | McKay |
| 5,981,828 A | 11/1999 | Nelson et al. |
| 6,022,509 A | 2/2000 | Matthews et al. |
| 6,030,635 A | 2/2000 | Gertzman et al. |
| 6,030,636 A | 2/2000 | Randolph et al. |
| 6,037,519 A | 3/2000 | McKay |
| 6,051,247 A | 4/2000 | Hench et al. |
| 6,056,970 A | 5/2000 | Greenawalt et al. |
| 6,071,530 A | 6/2000 | Polson et al. |
| 6,083,522 A | 7/2000 | Chu et al. |
| 6,117,456 A | 9/2000 | Lee et al. |
| 6,118,043 A | 9/2000 | Nies et al. |
| 6,136,029 A | 10/2000 | Johnson et al. |
| 6,149,688 A | 11/2000 | Brosnahan et al. |
| 6,206,957 B1 | 3/2001 | Driessens et al. |
| 6,214,368 B1 | 4/2001 | Lee et al. |
| 6,224,635 B1 | 5/2001 | Ricci et al. |
| 6,296,667 B1 | 10/2001 | Johnson et al. |
| 6,334,856 B1 | 1/2002 | Allen et al. |

(56) References Cited

U.S. PATENT DOCUMENTS

| | | |
|---|---|---|
| 6,340,477 B1 | 1/2002 | Anderson |
| 6,358,532 B2 | 3/2002 | Starling et al. |
| 6,425,949 B1 | 7/2002 | Lemaitre et al. |
| 6,527,810 B2 | 3/2003 | Johnson et al. |
| 6,537,589 B1 | 3/2003 | Chae et al. |
| 6,558,709 B2 | 5/2003 | Higham |
| 6,582,228 B2 | 6/2003 | Ricci et al. |
| 6,642,285 B1 | 11/2003 | Bohner |
| 6,652,887 B1 | 11/2003 | Richelsoph et al. |
| 6,733,582 B1 | 5/2004 | Bohner et al. |
| 6,753,007 B2 | 6/2004 | Haggard et al. |
| 6,793,725 B2 | 9/2004 | Chow et al. |
| 6,808,561 B2 | 10/2004 | Genge et al. |
| 6,822,033 B2 | 11/2004 | Yu et al. |
| 6,840,995 B2 | 1/2005 | Lin et al. |
| 6,849,275 B2 | 2/2005 | Higham |
| 6,949,251 B2 | 9/2005 | Dalal et al. |
| 6,953,594 B2 | 10/2005 | Lee et al. |
| 6,955,716 B2 | 10/2005 | Xu et al. |
| 6,994,726 B2 | 2/2006 | Lin et al. |
| 7,018,460 B2 | 3/2006 | Xu et al. |
| 7,211,266 B2 | 5/2007 | Cole et al |
| 7,371,408 B1 | 5/2008 | Petersen et al. |
| 7,371,409 B2 | 5/2008 | Petersen et al. |
| 7,417,077 B2 | 8/2008 | Lidgren et al. |
| 7,473,312 B2 | 1/2009 | Barralet et al. |
| 7,670,419 B2 | 3/2010 | Bohner |
| 7,754,246 B2 * | 7/2010 | Moseley et al. ............... 424/602 |
| 8,025,903 B2 * | 9/2011 | Moseley et al. ............... 424/602 |
| 2001/0018614 A1 | 8/2001 | Bianchi |
| 2001/0031799 A1 | 10/2001 | Shimp |
| 2002/0016636 A1 | 2/2002 | Ricci et al. |
| 2002/0055143 A1 | 5/2002 | Bell et al. |
| 2002/0169066 A1 | 11/2002 | Cassidy et al. |
| 2002/0197315 A1 | 12/2002 | Haggard et al. |
| 2003/0049328 A1 | 3/2003 | Dalal et al. |
| 2003/0050710 A1 | 3/2003 | Petersen et al. |
| 2003/0055512 A1 | 3/2003 | Genin et al. |
| 2003/0161852 A1 | 8/2003 | Miller et al. |
| 2003/0167093 A1 | 9/2003 | Xu et al. |
| 2003/0185903 A1 | 10/2003 | Cole et al. |
| 2003/0216777 A1 | 11/2003 | Tien et al. |
| 2004/0024081 A1 | 2/2004 | Trieu et al. |
| 2004/0048947 A1 | 3/2004 | Lidgren et al. |
| 2004/0137032 A1 | 7/2004 | Wang |
| 2004/0220681 A1 | 11/2004 | Cole et al. |
| 2004/0230309 A1 | 11/2004 | DiMauro et al. |
| 2004/0244651 A1 | 12/2004 | Lemaitre et al. |
| 2005/0031704 A1 | 2/2005 | Ahn |
| 2005/0042210 A1 | 2/2005 | Akai |
| 2005/0074415 A1 | 4/2005 | Chow et al. |
| 2005/0076813 A1 | 4/2005 | Lin et al. |
| 2005/0081750 A1 | 4/2005 | Xu et al. |
| 2005/0084542 A1 | 4/2005 | Rosenberg et al. |
| 2005/0119746 A1 | 6/2005 | Lidgren |
| 2005/0124720 A1 | 6/2005 | Rizzoli et al. |
| 2005/0170012 A1 | 8/2005 | Dalal et al. |
| 2005/0184418 A1 | 8/2005 | Lin et al. |
| 2005/0186353 A1 | 8/2005 | Lin et al. |
| 2005/0186449 A1 | 8/2005 | Lin et al. |
| 2005/0251149 A1 | 11/2005 | Wenz |
| 2005/0268819 A1 | 12/2005 | Lin et al. |
| 2006/0122706 A1 | 6/2006 | Lo |
| 2006/0213398 A1 | 9/2006 | Barralet et al. |
| 2007/0059281 A1 | 3/2007 | Moseley et al. |
| 2008/0206300 A1 | 8/2008 | Bohner et al. |
| 2009/0318982 A1 | 12/2009 | Genin et al. |
| 2012/0045484 A1 | 2/2012 | Cooper |

FOREIGN PATENT DOCUMENTS

| | | |
|---|---|---|
| WO | WO 89/07917 A1 | 9/1989 |
| WO | WO 91/00252 A1 | 1/1991 |
| WO | WO 91/17722 A1 | 11/1991 |
| WO | WO 96/39203 A1 | 12/1996 |
| WO | WO 98/22041 A1 | 5/1998 |
| WO | WO 98/40113 A1 | 9/1998 |
| WO | WO 99/15150 A1 | 4/1999 |
| WO | WO 99/16478 A1 | 4/1999 |
| WO | WO 99/16479 A1 | 4/1999 |
| WO | WO 99/17710 A1 | 4/1999 |
| WO | WO 99/49906 A1 | 10/1999 |
| WO | WO 00/07639 A1 | 2/2000 |
| WO | WO 00/74690 A1 | 12/2000 |
| WO | WO 01/12106 A1 | 2/2001 |
| WO | WO 02/05750 A2 | 1/2002 |
| WO | WO 02/05861 A1 | 1/2002 |
| WO | WO 02/32827 A1 | 4/2002 |
| WO | WO 02/068009 A2 | 9/2002 |
| WO | WO 02/087649 A1 | 11/2002 |
| WO | WO 03/024316 A2 | 3/2003 |
| WO | WO 03/030956 A2 | 4/2003 |
| WO | WO 03/053488 A1 | 7/2003 |
| WO | WO 2004/000374 A1 | 12/2003 |
| WO | WO 2004/101013 A1 | 11/2004 |
| WO | WO 2004/103419 A1 | 12/2004 |
| WO | WO 2005/084726 A1 | 9/2005 |
| WO | WO 2005/117919 A2 | 12/2005 |
| WO | WO 2006/014886 A2 | 2/2006 |
| WO | WO 2006/082442 A1 | 8/2006 |

OTHER PUBLICATIONS

Alge et al., Biomed. Mater. (2013), vol. 8, pp. 1-8.*
Bohner et al., "Effects of Sulfate Ions on the In Vitro Properties of β-TCP-MCPM-Water Mixtures. Preliminary In Vivo Results," Ceramic Transactions (1995) 48:245-259.
Bohner et al., "Effects of Sulfate, Pyrophosphate, and Citrate Ions on the Physicochemical Properties of Cements Made of β-Tricalcium Phosphate-Phosphoric Acid-Water Mixtures," J. Am. Cer. Soc. (1996) 79:1427-1434.
Tadros et al.,"Linear Growth Rates of Calcium Sulfate Dihydrate Crystals in the Presence of Additives," J. Coll. Inter. Sci. (1979) 72:245-252.
"Bone Graft Substitutes Safe, Effective", AMA Science New Media Briefings, Dec. 6, 2001.
Adkisson et al., "Rapid Quantitative Bioassay of Osteoinduction", J. Orthop. Res., 2000, pp. 503-511, vol. 18.
Barralet et al., "Ionic Modification of Calcium Phosphate Cement Viscosity. Part II: Hypodermic Injection and Strength Improvement of Brushite Cement", Biomaterials, 2004, pp. 2197-2203, vol. 25.
Betz, Randal R., "Limitations of Autograft and Allograft: New Synthetic Solutions", Orthopedics, 2002, pp. s561-s570, vol. 25, Supplement 5.
Charrière et al., "Mechanical Characterization of Brushite and Hydroxyapatite Cements", Biomaterials, 2001, pp. 2937-2945, vol. 22.
Cleere,et al. "In-vitro Dissolution Characteristics of Calcium Phosphate/Calcium Sulphate Based Hybrid Biomaterials," Key Engineering Materials, 2004, pp. 585-588, vols. 254-256.
De Groot et al., "Bioceramics Consisting of Calcium Phosphate Salts", Biomaterials, 1980, pp. 47-50, vol. 1.
Eggli et al., "Porous Hydroxyapatite and Tricalcium Phosphate Cylinders with Two Different Pore Size Ranges Implated in the Cancellous Bone of Rabbits", Clinical Orthopaedics and Related Research, 1988, pp. 127-138, No. 232.
Flautre et al., "Bone Colonization of β-TCP Granules Incorporated in Brushite Cements", J. Biomed Mater. Res. 2002, pp. 413-417, vol. 63, No. 4.
Gbureck et al., "Ionic Modification of Calcium Phosphate Cement Viscosity. Part I: Hypodermic Injection and Strength Improvement of Apatite Cement", Biomaterials, 2004, pp. 2187-2195, No. 25.
Girardi et al., "The Effect of Bone Graft Extenders to Enhance the Performance of Iliac Crest Bone Grafts in Instrumented Lumbar Spine Fusion", Orthopedics, 2003, pp. s545-S596, vol. 26, No. 5.

(56) References Cited

OTHER PUBLICATIONS

Gisep et al., "Bioperformance of Injectable Inorganic Cements as Bone Substitutes", A dissertation submitted to the Swiss Federal Institute of Technology Zurich, 2004.
Gisep et al., "Calcium-Phosphate-Calcium-Sulphate Bone Cements Structure and Compression Strength after Setting", *European Cells and Materials*, 2004, pp. 34-35, vol. 7, Suppl. 2.
Greenwald et al.., "Bone-Graft Substitutes: Facts, Fictions, and Applications", *J. Bone Joint Surg.*, 2001, pp. 98-103, vol. 83-A, Supplement 2, Part 2.
Grimandi et al. "In vitro Evaluation of a New Injectable Calcium Phosphate Material," *J Biomed Mater Res*, 1998, pp. 660-666, vol. 39.
Hanker et al. "Setting of Composite Hydroxyapatite/Plaster Implants with Blood for Bone Reconstruction," *Proceedings of the 44th Annual Meeting of the Electron Microscopy Society of America*, 1986, pp. 328-329.
Hanker et al., "Scanning Electron Microscopy of Composite Hydroxylapatite/Plaster Implants for Bone Reconstruction", *Proc. 44th Mtg. Electron Microscopy Soc. of America*, 1986, pp. 326-327.
Hardouin et al., "New Injectable Composites for Bone Replacement", *Seminars in Musculoskeletal Radiology*, 1997, pp. 319-323, vol. 1, No. 2.
Hofmann et al., "Stearate Salts as Brushite Bone Cement Setting Retardants", *Key Engineering Materials*, 2005, pp. 19-22, vols. 284-286.
Hollinger et al., "Biodegradable Bone Repair Materials", *Clinical Orthopaedics and Related Research*, 1986, pp. 290-305, No. 207.
Ikenaga et al., "Biomechanical Characterization of a Biodegradable Calcium Phosphate Hydraulic Cement: A Comparison with Porous Biphasic Calcium Phosphate Ceramics", *J. Biomed Mater. Res.*, 1998, pp. 139-144, vol. 40.
Kelly, Evelyn B., "New Frontiers in Bone Grafting", *Orthopedic Technology Review*, 2000, vol. 2, No. 9.
Komath et al., "Development of a Fully Injectable Calcium Phosphate Cement for Orthopedic and Dental Applications", *Bull. Mater. Sci.*, 2003, pp. 415-422, vol. 26, No. 4.
Kurashina et al., "Calcium Phosphate Cement: in vitro and in vivo studies of the α-tricalcium phosphate-dicalcium phosphate dibasic-tetracalcium phosphate monoxide system", *J. Mater. Sci..*, 1995, pp. 340-347, No. 6.
Landuyt et al., "Synthesis of β-Tricalcium Phosphate Powder with Controlled Specific Surface Area", *Bioceramics*, pp. 205-208, vol. 9, (1996).
Lemaitre, J., "Injectable Calcium Phosphate Hydraulic Cements: New Developments and Potential Applications", *Innov. Tech. Biol. Med.*, 1995, pp. 110-120, vol. 16.
Lemaitre et al., "Synthesis of β-Tricalcium Phosphate Powder with Controlled Specific Surface Area", *Bioceramics*, pp. 205-207, vol. 9, (1996).
Lemaitre et al., "Setting, hardening and resorption of calcium phosphate hydraulic cements", *Communications*, 1992, pp. 163-165, vol. 93, No. 3.
Leroux et al., "Effects of Various Adjuvants (Lactic Acid, Glycerol, and Chitosan) on the Injectability of a Calcium Phosphate Cement", *Bone*, 1999, vol. 25, No. 2.
Mirtchi et al., "Calcium Phosphate Cements: Action of Setting Regulators on the Properties of the β-tricalcium phosphate-Monocalcium Phosphate Cements" *Biomaterials*, 1989, pp. 634-638, vol. 10.

Munting et al., "Bone repair of defects filled with a phosphocalcic hydraulic cement: an in vivo study", *Journal of Materials Science: Materials in Medicine*, 1993, pp. 337-344, No. 4.
Nadkarni et al., "An In Vivo Evaluation of Calcium Sulfate Composite Graft Materials Using Rabbit Metaphyseal and Calvarial Defects", Poster Sesion—Bone Grafts—Valencia D, 46th Annual Meeting Orthopaedic Research Society, Mar. 12-15, 2000, Orlando, Florida, p. 0683.
Nilsson et al., "Biodegradation and Biocompatability of a Calcium Sulphate-hydroxyapatite Bone Substitute", *J. Bone and Joint Surgery*, 2004, pp. 120-125, vol. 86-B, No. 1.
Nilsson et al., "Factors Influencing the Compressive Strength of an Injectable Calcium Sulfate-Hydroxyapatite Cement," *Journal of Material Science: Materials in Medicine*, 2003, pp. 399-404, vol. 14.
Nilsson et al., "Injectable Calcium Sulphate and Calcium Phosphate Bone Substitutes", Thesis, Lund University, Faculty of Medicine, Lund, Sweden, Apr. 2003, pp. 1-41.
Ohura et al., "Resorption of, and bone formation from, new β-tricalcium phosphate-monocalcium phosphate cements: An in vivo study", *J. Biomedical Materials Research*, 1996, pp. 193-200, vol. 30.
Pioletti et al., "The Effects of Calcium Phosphate Cement Particles on Osteoblast Functions", *Biomaterials*, 2000, pp. 1103-1114, vol. 21.
Sarda et al., "Rheological Properties of an Apatitic Bone Cement During Initial Setting", *J. Mater. Sci.*, 2001, pp. 905-909, vol. 12.
Sato et al. "Osteogenic Response of Rabbit Tibia to Hydroxyapatite Particle—Plaster of Paris Mixture," *Biomaterials*, 1998, pp. 1895-1900, vol. 19.
Sawamura et al., "Effects of Polysaccharides Addition in Calcium Phosphate Cement", *Key Engineering Materials*, 2004, pp. 209-212, vols. 254-256.
Shimazaki et al., "Comparative Study of Porous Hydroxyapatite and Tricalcium Phosphate as Bone Substitute", *J. Orthop Res.*, 1985, pp. 301-310, vol. 3, No. 3.
Theiss et al., "The Use of a Bioresorbable Calcium Phosphate Cement in Partial Tibial Plateau Defects in Sheep", *European Cells and Materials*, 2001, pp. 32-33, vol. 1, Supp. 1.
Turner et al., "Radiographic and Histologic Assessment of Calcium Sulfate in Experimental Animal Models and Clinical Use as a Resorbable Bone-Graft Substitute, a Bone-Graft Expander, and a Method for Local Antibiotic Delivery", *J. Bone Joint Surg.*, 2001, pp. 8-18., vol. 83-A.
Turner et al., "Restoration of Large Bone Defects Using a Hard-Setting, Injectable Putty Containing Demineralized Bone Particles Compared to Cancellous Autograft Bone", *Orthopedics*, 2003, pp. s561-s579, vol. 26, No. 5.
Urban et al., "Healing of Large Defects Treated With Calcium Sulfate Pellets Containing Demineralized Bone Matrix Particles", *Orthopedics*, 2003, pp. s582-s585, vol. 26, No. 5.
Van Der Houwen et al., "The Application of Calcium Phosphate Precipitation Chemistry to Phosphorus Recovery: The Influence of Organic Ligands", *Environmental Technology*, 2001, pp. 1325-1335, vol. 22, Selper Ltd.
STN online, file SCISEARCH, Acc. No. 1992:243308 (Hill, Radiation Physics and Chemistry (1992); vol. 39, No. 3, pp. 237-241), Abstract.
Gbureck et al., Factors influencing calcium phosphate cement shelf-life, Biomaterials (2005), vol. 26, pp. 3691-3697.

\* cited by examiner

Top and Bottom View

Side View

Front and Rear Views

COMPOSITE BONE GRAFT SUBSTITUTE CEMENT AND ARTICLES PRODUCED THEREFROM

CROSS REFERENCE TO RELATED APPLICATIONS

This application is a continuation of U.S. application Ser. No. 11/530,085, filed Sep. 8, 2006, now U.S. Pat. No. 7,754, 246 which claims priority to U.S. Provisional Patent Application Ser. No. 60/715,542, filed Sep. 9, 2005, both of which are incorporated herein by reference in their entirety and for all purposes.

FIELD OF THE INVENTION

The invention is directed to a particulate composition adapted for forming a bone graft substitute cement upon mixing with an aqueous solution, a bone graft substitute cement made therefrom, a bone graft substitute kit comprising the particulate composition, methods of making and using the particulate composition, and articles made from the bone graft substitute cement.

BACKGROUND OF THE INVENTION

Defects in bone structure arise in a variety of circumstances, such as trauma, disease, and surgery. There is a need for effective repair of bone defects in various surgical fields, including maxillo-craniofacial, periodontics, and orthopedics. Numerous natural and synthetic materials and compositions have been used to stimulate healing at the site of a bone defect. As with compositions used to repair other types of tissue, the biological and mechanical properties of a bone repair material are critical in determining the effectiveness and suitability of the material in any particular application.

After blood, bone is the second most commonly transplanted material. Autologous cancellous bone has long been considered the most effective bone repair material, since it is both osteoinductive and non-immunogenic. However, adequate quantities of autologous cancellous bone are not available under all circumstances, and donor site morbidity and trauma are serious drawbacks to this approach. The use of allograft bone avoids the problem of creating a second surgical site in the patient, but suffers from some disadvantages of its own. For instance, allograft bone typically has a lower osteogenic capacity than autograft bone, a higher resorption rate, creates less revascularization at the site of the bone defect, and typically results in a greater immunogenic response. The transfer of certain diseases is also a danger when using allografts.

To avoid the problems associated with autograft and allograft bone, considerable research has been conducted in the area of synthetic bone substitute materials that can be used in lieu of natural bone. For example, various compositions and materials comprising demineralized bone matrix, calcium phosphate, and calcium sulfate have been proposed.

Cements comprising calcium sulfate have a long history of use as bone graft substitutes. Modern surgical grade calcium sulfate cements offer high initial strength, good handling properties, and are consistently replaced by bone in many applications. However, calcium sulfate cements are characterized by relatively rapid resorption by the body, which can be undesirable in certain applications.

Hydroxyapatite is one of the most commonly used calcium phosphates in bone graft materials. Its structure is similar to the mineral phase of bone and it exhibits excellent biocompatibility. However, hydroxyapatite has an extremely slow resorption rate that may be unsuitable in certain applications. Other calcium phosphate materials have also been used in the art, such as β-tricalcium phosphate, which exhibits a faster resorption rate than hydroxyapatite, but has less mechanical strength. Certain calcium phosphate materials that set in situ have also been attempted, such as mixtures of tetracalcium phosphate and dicalcium phosphate anhydrate or dihydrate, which react to form hydroxyapatite when mixed with an aqueous solution.

The presently available synthetic bone repair materials do not present ideal functional characteristics for all bone graft applications. As noted above, some compositions exhibit a resorption rate that is either too slow or too rapid. Further, many bone graft cements are difficult to implant because they fail to set or cannot be injected. Other drawbacks are inadequate strength and difficulty in adding biologically active substances for controlled release. For these reasons, there remains a need in the art for bone graft cement compositions that combine a desirable resorption rate with high mechanical strength, ease of handling, and osteoconductivity.

BRIEF SUMMARY OF THE INVENTION

The present invention provides a particulate composition adapted for forming a bone graft substitute cement upon mixing with an aqueous solution, as well as a hardened bone graft substitute cement made therefrom. The invention also relates to kits comprising the particulate composition, and methods of making and using the composition. The particulate composition of the invention comprises a calcium sulfate hemihydrate powder in combination with a brushite-forming calcium phosphate mixture. Upon mixing the particulate composition with an aqueous mixing solution, a hardened biphasic cement comprising brushite and calcium sulfate dihydrate is formed. The calcium sulfate dihydrate provides good mechanical strength and, due to its relatively fast resorption rate, is rapidly replaced with bone tissue in the resulting cement, while the brushite serves to reduce the overall resorption rate of the cement as compared to a cement composition solely comprising calcium sulfate dihydrate. Certain embodiments of the bone substitute cement of the invention exhibit high mechanical strength, such as high compressive strength and diametral tensile strength, set into a hardened composition within a reasonable period of time, facilitate development of high quality bone at the site of the bone defect, and exhibit acceptable handling characteristics.

In one aspect, the invention provides a particulate composition comprising a mixture of a calcium sulfate hemihydrate powder having a bimodal particle distribution and a median particle size of about 5 to about 20 microns, and a brushite-forming calcium phosphate composition. The brushite-forming calcium phosphate mixture comprises monocalcium phosphate monohydrate powder and a β-tricalcium phosphate powder. The β-tricalcium phosphate powder has a median particle size of less than about 20 microns. The calcium sulfate hemihydrate powder is present at a concentration of at least about 50 weight percent based on the total weight of the particulate composition, more preferably at least about 70 weight percent, and most preferably at least about 75 weight percent. The brushite-forming calcium phosphate composition is typically present at a concentration of about 3 to about 30 weight percent based on the total weight of the particulate composition.

The β-tricalcium phosphate powder portion of the particulate composition preferably has a bimodal particle size distribution characterized by about 30 to about 70 volume percent of particles having a mode of about 2.0 to about 6.0 microns and about 30 to about 70 volume percent of particles having a mode of about 40 to about 70 microns based on the total volume of the β-tricalcium phosphate powder. In another embodiment, the bimodal particle size distribution comprises about 50 to about 65 volume percent of particles having a mode of about 4.0 to about 5.5 microns and about 35 to about 50 volume percent of particles having a mode of about 60 to about 70 microns based on the total volume of the β-tricalcium phosphate powder.

The calcium sulfate hemihydrate portion of the particulate composition preferably comprises α-calcium sulfate hemihydrate, and the bimodal particle distribution preferably comprises about 30 to about 60 volume percent of particles having a mode of about 1.0 to about 3.0 microns, and about 40 to about 70 volume percent of particles having a mode of about 20 to about 30 microns, based on the total volume of the calcium sulfate hemihydrate powder.

The particulate composition mixture may further comprise β-tricalcium phosphate granules having a median particle size of at least about 75 microns, such as about 75 to about 1,000 microns. The β-tricalcium phosphate granules are typically present at a concentration of up to about 20 weight percent based on the total weight of the particulate composition, and more preferably at a concentration of up to about 12 weight percent.

The particulate composition may comprise further additives, such as an accelerant adapted for accelerating the conversion of calcium sulfate hemihydrate to calcium sulfate dihydrate. An example of such an accelerant is sucrose-coated calcium sulfate dihydrate particles. Further, the composition may comprise a biologically active agent, such as cancellous bone chips, growth factors, antibiotics, pesticides, chemotherapeutic agents, antivirals, analgesics, anti-inflammatory agents, and osteoinductive or osteoconductive materials. Demineralized bone matrix is one preferred biologically active agent.

In one embodiment, the particulate composition of the invention sets to a hardened mass upon mixing with an aqueous solution in about 3 to about 25 minutes. Thus, in another aspect of the invention, a bone graft substitute cement is provided, the cement comprising the paste formed by mixing the particulate composition of the invention with an aqueous solution. The bone graft substitute cement can comprise β-tricalcium phosphate granules (if present) and a reaction product formed by mixing a particulate composition of the invention with an aqueous solution, the reaction product comprising calcium sulfate dihydrate and brushite. The bone graft substitute cement can be cast in a predetermined shape, such as pellets, granules, wedges, blocks, and disks, molded into a desired shape at the time of application, or simply injected or otherwise delivered to the site of a bone defect without prior molding or shaping. The cement of the invention can also be incorporated into any of various orthopedic implant devices, typically being applied in the form of outer coatings or as filling material in porous outer layers of such devices in order to facilitate bone ingrowth in the area of the implanted device.

The hardened bone graft substitute cement preferably exhibits certain mechanical strength characteristics, such as a diametral tensile strength of at least about 4 MPa after curing for one hour in ambient air following mixing of the particulate composition with an aqueous solution, more preferably a diametral tensile strength of at least about 5 MPa, most preferably at least about 6 MPa. Further, preferred embodiments of the bone graft substitute cement exhibit a diametral tensile strength of at least about 8 MPa after curing for 24 hours in ambient air following mixing of the particulate composition with an aqueous solution, more preferably a diametral tensile strength of at least about 9 MPa after curing for 24 hours, and most preferably at least about 10 MPa.

Preferred embodiments of the bone graft substitute cement also exhibit a high level of compressive strength, such as a compressive strength of at least about 15 MPa after curing for one hour in ambient air following mixing of the particulate composition with an aqueous solution, more preferably a compressive strength of at least about 40 MPa. Further, preferred embodiments of the bone graft substitute cement will exhibit a compressive strength of at least about 50 MPa after curing for 24 hours in ambient air following mixing of the particulate composition with an aqueous solution, more preferably a compressive strength of at least about 80 MPa.

Preferred embodiments of the bone graft substitute cement also exhibit an average dissolution rate, expressed as an average percentage of weight loss per day, that is at least about 25% lower than the average dissolution rate of a cement formed using a particulate composition consisting of calcium sulfate, the average dissolution rate measured by immersion of a 4.8 mm OD pellet having a length of 3.3 mm in distilled water at 37° C. More preferably, the average dissolution rate is at least about 30% lower or at least about 35% lower.

In yet another aspect, the present invention provides a bone graft substitute kit, comprising at least one container enclosing the particulate composition according to the invention, a separate container enclosing a sterile aqueous solution, and a written instruction set describing a method of using the kit. The bone graft substitute kit may further comprise a mixing apparatus for mixing the aqueous solution with the particulate composition, and a device for delivering the bone graft substitute cement to the site of a bone defect, such as an injection device (e.g., a syringe).

In a further aspect of the invention, a method for treating a bone defect is provided. The method comprising applying the above-described bone graft substitute cement to the site of the bone defect. As noted above, the bone graft substitute cement can be administered in the form of a precast molded form, molded immediately prior to administration into the desired shaped based on the size and shape of the bone defect, or administered using an injection device or other means of delivering the composition directly to the bone defect without prior molding.

In a still further aspect of the invention, a method of forming the particulate composition of the invention is provided. The method typically comprises mixing or blending each powder or granule component of the particulate composition in order to form a homogenous mixture. Thus, in one embodiment, the method of forming the particulate composition comprises mixing the β-tricalcium phosphate powder, the calcium sulfate hemihydrate powder (which can be optionally accelerated by the addition of an accelerant as noted above), monocalcium phosphate monohydrate powder, and β-tricalcium phosphate granules (if present). The mixing of the various powder or granular ingredients preferably occurs immediately prior to mixing of the particulate composition with the aqueous solution.

The aqueous solution mixed with the particulate composition in order to form the setting cement preferably comprises sterile water, and may include at least one carboxylic acid therein. For example, the carboxylic acid can be glycolic acid or other hydroxy carboxylic acids. Preferably, the acid is neutralized to a neutral pH of approximately 6.5-7.5.

In another aspect of the invention, methods, compositions, and kits are provided for enhancing the storage stability of the components of the bone graft substitute composition of the invention. In one embodiment, the brushite-forming calcium phosphate materials (i.e., β-tricalcium phosphate powder and monocalcium phosphate monohydrate powder) are either stored separately prior to preparation of the bone graft substitute cement (e.g., placed in separate containers in a kit) or hermetically packaged in a completely dry environment in order to prevent reaction of the two calcium phosphate compounds. In another embodiment, the organic carboxylic acid component discussed above in connection with the aqueous mixing solution is packaged as a crystalline powder (e.g., in neutralized salt form such as an alkali metal salt) with the remaining particulate components of the kit rather than in solution. Using the acid component in powder form avoids degradation of the acid upon sterilization of the composition with gamma radiation, which can lead to undesirable increases in the setting time of the bone graft substitute cement of the invention.

Thus, in one embodiment, the invention provides a method for improving the storage stability of a kit comprising a particulate composition and an aqueous solution adapted for forming a bone graft substitute cement upon mixing, wherein the kit includes calcium phosphate powders reactive to form brushite in the presence of water and a carboxylic acid, the method comprising: i) packaging a monocalcium phosphate monohydrate powder and a β-tricalcium phosphate powder in separate containers in the kit; and ii) packaging the carboxylic acid in the kit either in the form of a crystalline powder or dissolved in the aqueous solution, with the proviso that when the carboxylic acid is dissolved in the aqueous solution, it is added to the solution after radiation sterilization of the aqueous solution. The kit may further comprise calcium sulfate hemihydrate powder, and the method may further comprise packaging the calcium sulfate hemihydrate powder in a separate container, or in admixture with one or both of the monocalcium phosphate monohydrate powder and the β-tricalcium phosphate powder. The method will typically further comprise irradiating the components of the kit with gamma radiation for sterilization.

Exemplary neutralized salts of carboxylic acids that can be utilized as the carboxylic acid powder include sodium glycolate, potassium glycolate, sodium lactate, and potassium lactate. The carboxylic acid crystalline powder is typically packaged separately in a container or packaged in the container containing the monocalcium phosphate monohydrate powder or in the container containing the β-tricalcium phosphate powder.

In another embodiment of the invention, a bone graft substitute kit is provided, comprising: i) a first container enclosing a monocalcium phosphate monohydrate powder; ii) a second container enclosing a β-tricalcium phosphate powder; iii) a calcium sulfate hemihydrate powder enclosed within a separate container or admixed with one or both of the monocalcium phosphate monohydrate powder and the β-tricalcium phosphate powder; iv) an aqueous solution enclosed within a separate container; and v) a carboxylic acid dissolved within the aqueous solution or present in the form of a crystalline powder, the carboxylic acid crystalline powder being enclosed within a separate container or admixed with any one or more of the monocalcium phosphate monohydrate powder, the β-tricalcium phosphate powder, and the calcium sulfate hemihydrate powder, with the proviso that when the carboxylic acid is dissolved in the aqueous solution, it is added to the solution after radiation sterilization of the aqueous solution. In certain embodiments, the carboxylic acid crystalline powder is enclosed within a separate container such that the carboxylic acid crystalline powder can be reconstituted by admixture with the aqueous solution prior to mixing the aqueous solution with one or more of the monocalcium phosphate monohydrate powder, the β-tricalcium phosphate powder, and the calcium sulfate hemihydrate powder.

The calcium sulfate hemihydrate powder may further include, in admixture, an accelerant adapted for accelerating the conversion of calcium sulfate hemihydrate to calcium sulfate dihydrate. Additionally, the kit may further include β-tricalcium phosphate granules in a separate container or in admixture with one or more of the monocalcium phosphate monohydrate powder, the β-tricalcium phosphate powder, and the calcium sulfate hemihydrate powder. A biologically active agent can also be included in the kit and enclosed within a separate container or admixed with any one or more of the monocalcium phosphate monohydrate powder, the β-tricalcium phosphate powder, and the calcium sulfate hemihydrate powder.

In yet another embodiment, a bone graft substitute kit is provided, comprising: i) a first container enclosing a monocalcium phosphate monohydrate powder; ii) a second container enclosing β-tricalcium phosphate powder having a median particle size of less than about 20 microns; iii) an α-calcium sulfate hemihydrate powder enclosed within a separate container or admixed with the β-tricalcium phosphate powder in the second container, the α-calcium sulfate hemihydrate powder having a bimodal particle distribution and a median particle size of about 5 to about 20 microns; iv) an aqueous solution enclosed within a separate container; v) a carboxylic acid in the form of a crystalline powder, the carboxylic acid crystalline powder being enclosed within a separate container, wherein the carboxylic acid is in the form of a neutralized alkali metal salt; vi) an accelerant adapted for accelerating the conversion of calcium sulfate hemihydrate to calcium sulfate dihydrate in admixture with the α-calcium sulfate hemihydrate powder; and vii) β-tricalcium phosphate granules in a separate container or in admixture with one or both of the β-tricalcium phosphate powder and the calcium sulfate hemihydrate powder, wherein the granules have a median particle size of at least about 75 microns.

BRIEF DESCRIPTION OF THE DRAWINGS

Figure 1:
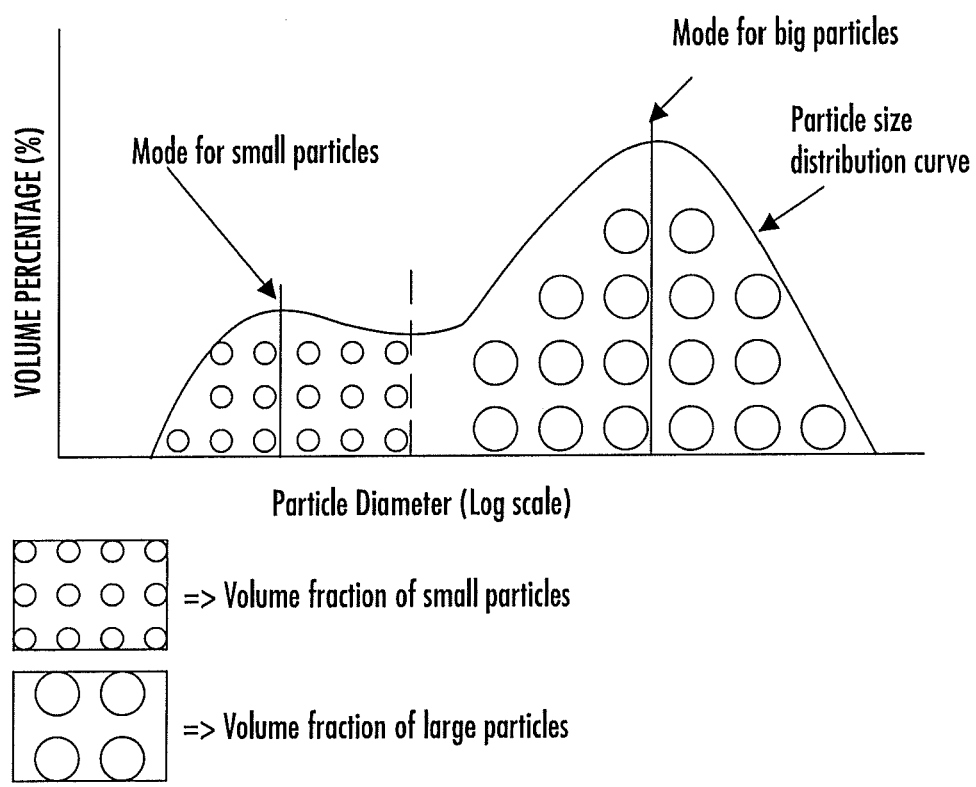
Figure 2A:
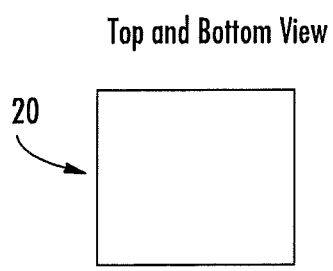
Figure 2B:
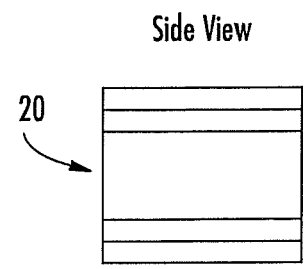
Figure 2C:
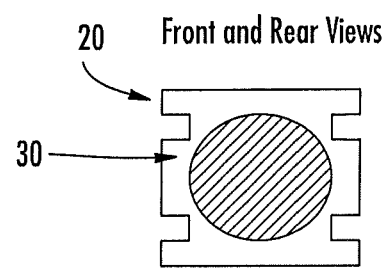
Figure 3:
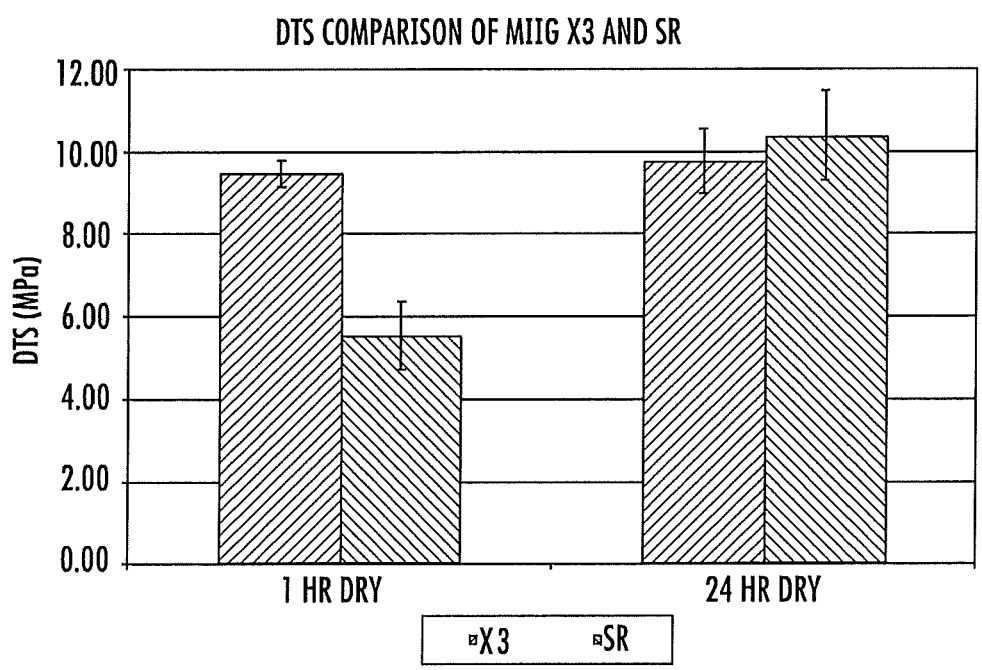
Figure 4:
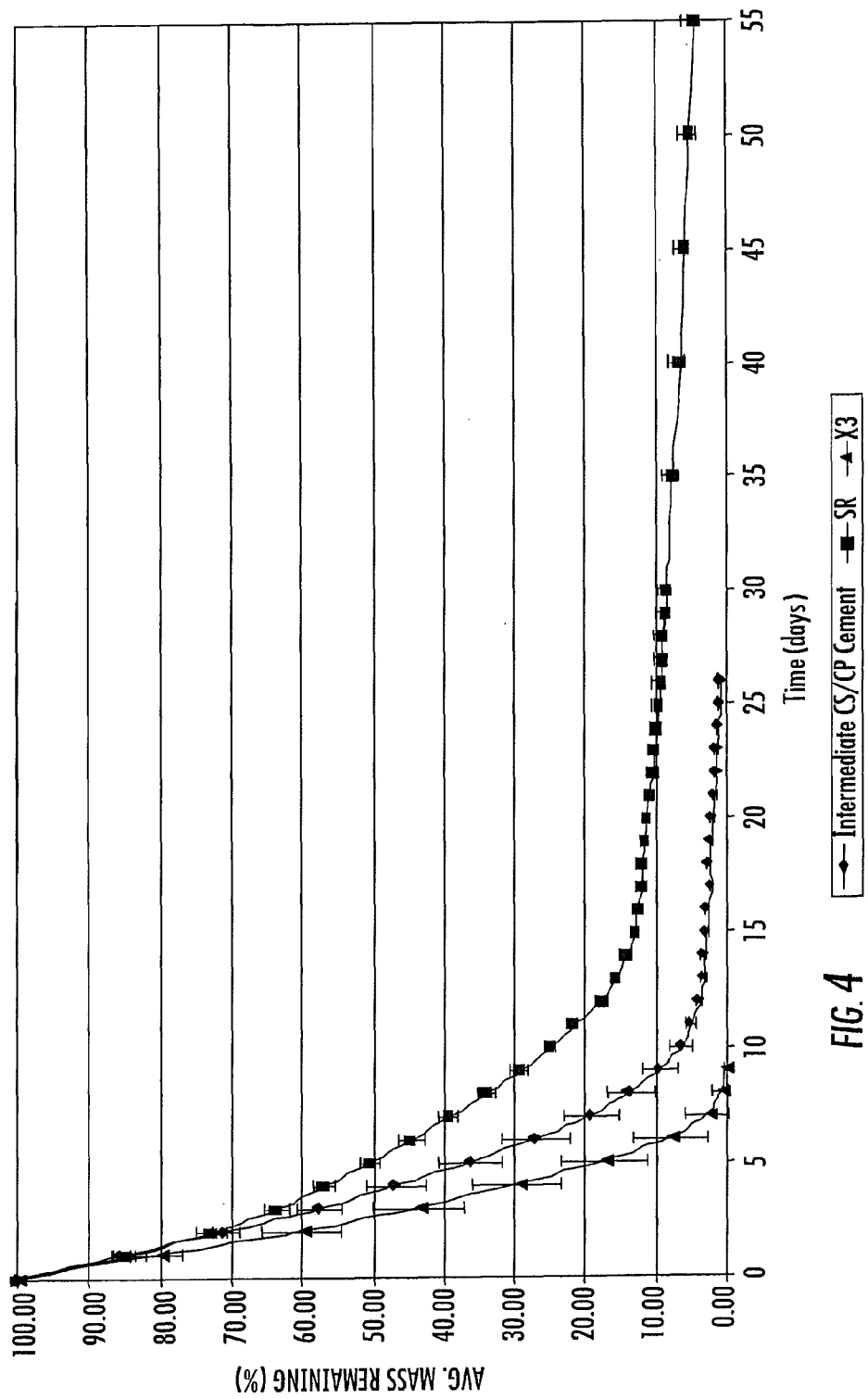
Figure 5:
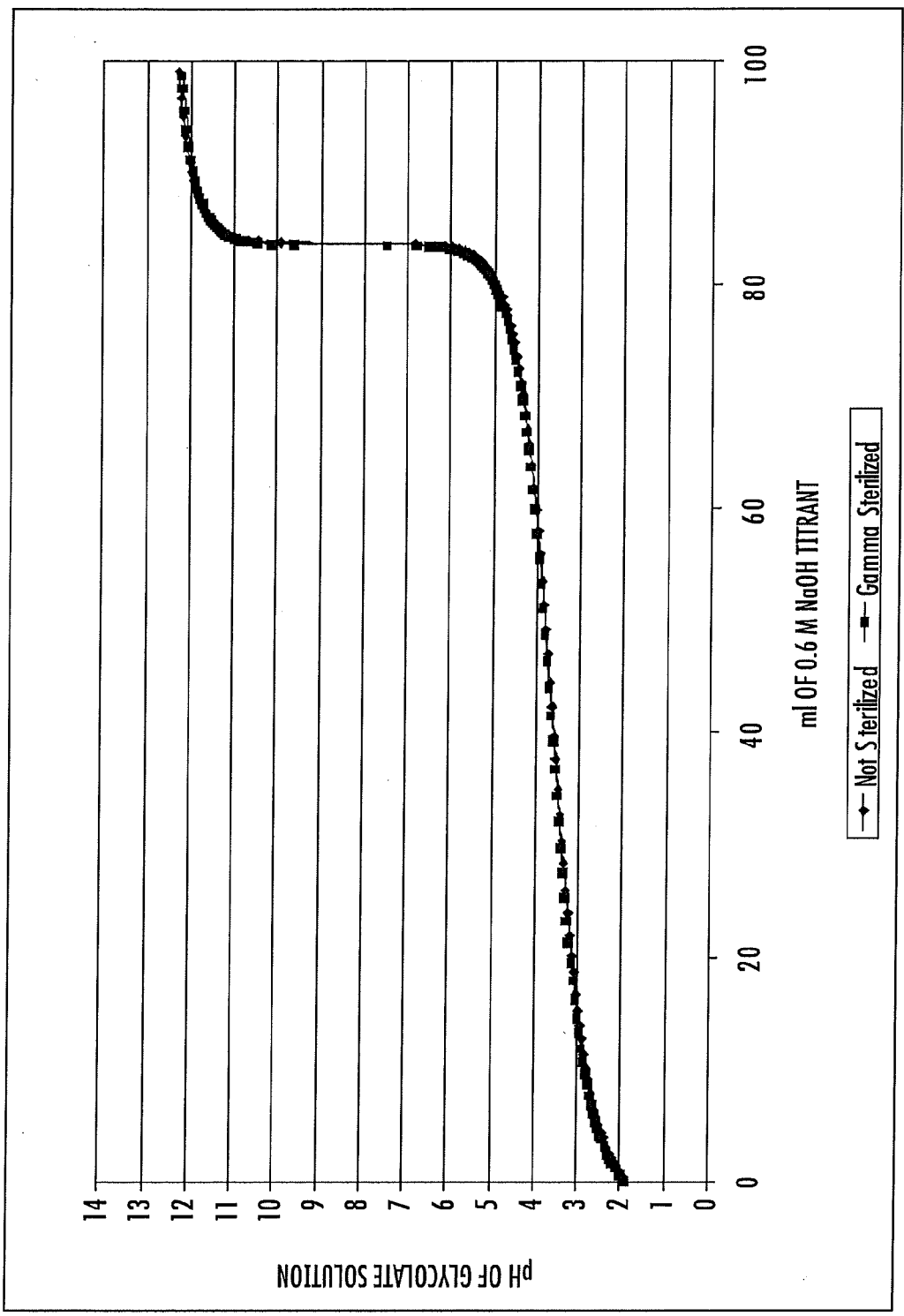

Having thus described the invention in general terms, reference will now be made to the accompanying drawings, wherein:

FIG. 1 graphically illustrates the concept of a bimodal particle size distribution plot based on high resolution laser diffraction;

FIGS. 2a, 2b, and 2c provide several views of an exemplary diametral tensile strength specimen mold;

FIG. 3 graphically illustrates a comparison of diametral tensile strength of a bone graft cement according to the invention and a commercially available calcium sulfate cement;

FIG. 4 graphically illustrates the in vitro dissolution properties of two bone graft cements according to the invention as compared to a commercially available calcium sulfate cement; and FIG. 5 graphically illustrates titration curves for solutions made using non-irradiated and gamma irradiated crystalline glycolic acid.

DETAILED DESCRIPTION OF THE INVENTION

The present inventions now will be described more fully hereinafter with reference to the accompanying drawings. The invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The present invention provides a particulate composition useful as a bone graft substitute cement that hardens or sets upon mixing with an aqueous solution. The particulate composition includes a calcium sulfate hemihydrate (hereinafter "CSH") powder and a brushite-forming calcium phosphate mixture comprising monocalcium phosphate monohydrate (hereinafter "MCPM") powder and a β-tricalcium phosphate (hereinafter "β-TCP") powder.

Use of the particulate composition of the invention produces a bone graft substitute cement comprising calcium sulfate dihydrate (hereinafter "CSD"), which is the product of the reaction between CSH and water. The CSD component of the cement confers good mechanical strength to the cement, stimulates bone growth, and provides a relatively fast resorption rate in vivo, such that a porous structure in the cement is quickly created upon implantation. Thus, the CSD component of the cement can be rapidly replaced with bone tissue ingrowth into the implant site.

The two calcium phosphate components react to form brushite upon mixing with an aqueous solution. The presence of the brushite in the cement slows the resorption rate of the bone graft substitute cement as compared to a cement comprising CSD only. Thus, the biphasic bone graft substitute cement of the invention provides a dual resorption rate defined by the CSD component and the brushite component.

In addition to a slower resorption rate, embodiments of the particulate composition of the invention can provide a bone graft substitute cement that exhibits high mechanical strength, good handling characteristics, and a reasonable setting time. Additionally, certain embodiments of the bone graft substitute cement of the invention are capable of producing high quality bone when used to treat bone defects.

The CSH powder used in the present invention preferably has a bimodal particle distribution. As understood in the art, a bimodal particle distribution refers to a particle distribution characterized by two peaks in a plot of particle size vs. the volume percentage of particles of each size. FIG. 1 illustrates an exemplary bimodal particle size distribution plot. In a preferred embodiment, the bimodal particle distribution of the CSH powder is characterized by about 30 to about 60 volume percent of particles having a mode of about 1.0 to about 3.0 microns and about 40 to about 70 volume percent of particles having a mode of about 20 to about 30 microns, based on the total volume of the CSH powder. In yet another embodiment, the bimodal particle distribution comprises about 40 to about 60 volume percent of particles having a mode of about 1.0 to about 2.0 microns and about 40 to about 60 volume percent of particles having a mode of about 20 to about 25 microns. The median particle size of the CSH powder is preferably about 5 to about 20 microns, more preferably about 8 to about 15 microns, and most preferably about 10 to about 15 microns.

As used herein, "median particle size" refers to the particle size that divides a population of particles in half such that half of the volume of particles in the population is above the median size and half is below. Median particle size is measured using linear interpolation of data acquired through a high resolution laser diffraction method. More specifically, the laser diffraction method is performed with parallel light with a constant frequency of 632.8 nanometers and which exhibits 5 milliwatts of power. Measurements of laser diffraction are acquired through a 32 channel detector array. Particle delivery to measurement system is performed through a relatively constant mass flow rate using an optimum dispersing media such as air flow creating a −3.5 bar gauge pressure. A commercially available machine for laser-diffraction particle analysis is the OASIS (Sympatec; Clausthal-Zellerfeld, Germany) dispersing unit. The OASIS system is used in the dry mode via the VIBRI model HDD200 and RODOS M. The VIBRI model is used with a 75% feed rate and 3.0 mm gap. The −3.5 bar gauge pressure is produced through a 4 mm injector. For measuring particle size of calcium sulfate hemihydrate, the R2 lens (0.25/0.45 . . . 87.5 um) is preferred, and for tricalcium phosphate components, the R4 lens (0.5/1.8 . . . 350 um) is preferred (both also from Sympatec).

The particulate composition in the invention preferably comprises a CSH powder in an amount of at least about 50 weight percent based on the total weight of the particulate composition, more preferably at least about 70 weight percent, and most preferably at least about 75 weight percent. In certain embodiments, the CSH powder is present in an amount of at least about 80 weight percent, at least about 85 weight percent, or at least about 90 weight percent. Typically, the CSH powder is present in an amount of about 70 weight percent to about 99 weight percent, more preferably about 70 weight percent to about 90 weight percent.

The CSH is preferably α-calcium sulfate hemihydrate, which exhibits higher mechanical strength as compared to the beta form upon setting to form CSD. The CSH portion of the particulate composition is important for providing mechanical strength to the resulting bone graft substitute cement, as well as contributing to the ability to set or harden in a relatively short period of time. As is known in the art, CSH has the formula $CaSO_4 \cdot \frac{1}{2}H_2O$, and will react with water to form calcium sulfate dihydrate ($CaSO_4 \cdot 2H_2O$). It is believed that the presence of CSD in the bone graft substitute cement of the invention contributes to rapid regeneration of bone tissue at the site of the bone defect.

CSH powder can be formed by dehydration of the dihydrate form by heating. Depending on the method of heating, the alpha or beta form is obtained. The two forms exhibit crystallographic and particle morphology differences. The preferred alpha form, which has a higher density, is typically characterized by large, hexagonal shaped rod-like primary crystals that are compact and well formed with sharp edges.

In a preferred embodiment, the CSH powder is made by the process disclosed in U.S. Pat. No. 2,616,789, which is incorporated entirely herein by reference in its entirety. The process involves immersion of calcium sulfate dihydrate in a solution of water and an inorganic salt. Preferred salts include magnesium chloride, calcium chloride, and sodium chloride. However, other inorganic salts can be used without departing from the invention, such as ammonium chloride, ammonium bromide, ammonium iodide, ammonium nitrate, ammonium sulfate, calcium bromide, calcium iodide, calcium nitrate, magnesium bromide, magnesium iodide, magnesium nitrate, sodium bromide, sodium iodide, sodium nitrate, potassium chloride, potassium bromide, potassium iodide, potassium nitrate, cesium chloride, cesium nitrate, cesium sulfate, zinc chloride, zinc bromide, zinc iodide, zinc nitrate, zinc sulfate, cupric chloride, cupric bromide, cupric nitrate, cupric sulfate, and mixtures thereof. Preferred salts are biocompatible, and any of the salts can be used in their anhydrous or hydrate forms. Reference to the salt is intended to encompass both anhydrous and hydrate forms. The calcium sulfate dihydrate and the solution are heated to substantially the boiling point at atmospheric pressure until a substantial portion of the calcium sulfate dihydrate is converted to CSH. The resulting CSH has a different crystalline structure than CSH produced by other hydrothermal processes and has a lower water-carrying capacity after being milled. In particular, the crystalline structure of the CSH made according to this method is characterized by thick, stubby, rod-like crystals.

In one embodiment, the CSH powder further includes an accelerant capable of accelerating the conversion of CSH to the dihydrate form, thereby causing the bone graft substitute cement made therefrom to set more quickly. Although not wishing to be bound by a theory of operation, it is believed that the accelerant particles act as crystallization nucleation sites for the conversion of CSH to calcium sulfate dihydrate. Examples of accelerants include calcium sulfate dihydrate, potassium sulfate, sodium sulfate, or other ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, which is hereby incorporated by reference in its entirety. The accelerant is typically present in an amount of up to about 1.0 weight percent, based on the total weight of the particulate composition. In some embodiments, the particulate composition includes between about 0.001 and about 0.5 weight percent of the accelerant, more typically between about 0.01 and about 0.3 weight percent. Mixtures of two or more accelerants can be used.

The calcium phosphate portion of the particulate composition of the invention comprises a MCPM powder (Ca$(H_2PO_4)_2 \cdot H_2O$) and a β-TCP powder ($Ca_3(PO_4)_2$). As understood in the art, the main reaction product of MCPM and β-TCP is brushite, otherwise known as dicalcium phosphate dihydrate ($CaHPO_4 \cdot 2H_2O$) (DCPD). The brushite-forming powders may also participate in other reactions that would result in the formation of certain calcium phosphates with a greater thermodynamic stability than DCPD, such as hydroxyapatite, octacalcium phosphate, and the like. A certain amount of the β-TCP powder may also remain unreacted in the cement.

The β-TCP powder preferably has a median particle size of less than about 20 microns, and more preferably a median particle size of less than about 18 microns, and most preferably a median particle size of less than about 15 microns. Typically the β-TCP powder will have a median particle size of about 10 microns to about 20 microns. The size of the β-TCP powder may affect the amount of brushite formed in the bone graft substitute cement. It is believed that smaller particle sizes of β-TCP will result in an increased rate of brushite formation, and larger particle sizes will result in a lower rate of brushite formation. It is typically preferred to use smaller β-TCP particles in order to increase the brushite-forming reaction rate.

The β-TCP powder portion of the particulate composition preferably has a bimodal particle size distribution characterized by about 30 to about 70 volume percent of particles having a mode of about 2.0 to about 6.0 microns and about 30 to about 70 volume percent of particles having a mode of about 40 to about 70 microns based on the total volume of the β-tricalcium phosphate powder. In one embodiment, the β-TCP powder has a bimodal particle size distribution characterized by about 50 to about 65 volume percent of particles having a mode of about 4.0 to about 5.5 microns and about 35 to about 50 volume percent of particles having a mode of about 60 to about 70 microns based on the total volume of the β-tricalcium phosphate powder.

The MCPM powder is relatively soluble in water, which means particle size is relatively unimportant. Typically, the MCPM powder will have a particle size of less than about 350 microns; however, other particles size could be utilized without departing from the invention. As would be understood, MCPM is the hydrate form of monocalcium phosphate (MCP). As used herein, reference to MCPM is intended to encompass MCP, which is simply the anhydrous form of MCPM that releases the same number of calcium and phosphoric acid ions in solution. However, if MCP is used in place of MCPM, the amount of water used to form the bone graft substitute cement would need to be increased to account for the water molecule missing from MCP (if it is desired to produce precisely the same dissolution product as formed when using MCPM).

As noted above, the brushite component of the bone graft substitute cement of the invention serves to slow the in vivo resorption of the bone graft substitute cement as compared to a calcium sulfate cement. In turn, the slower resorption rate may enable the bone graft substitute cement to provide structural support at the site of the bone defect for longer periods of time, which can aid the healing process in certain applications. Although not bound by any particular theory of operation, it is believed that the bone graft substitute cement of the invention will become a highly porous matrix of calcium phosphate material after being administered in vivo due to the relatively quick resorption of the calcium sulfate component of the mixture. The remaining porous matrix of calcium phosphate provides excellent scaffolding for bone ingrowth during the natural healing process.

The amount of MCPM powder and β-TCP powder present in the particulate composition can vary and depends primarily on the amount of brushite desired in the bone graft substitute cement. The brushite-forming calcium phosphate composition (i.e., the combined amount of MCPM and β-TCP powders) will typically be present at a concentration of about 3 to about 30 weight percent based on the total weight of the particulate composition, more preferably about 10 to about 20 weight percent, most preferably about 15 weight percent. The relative amounts of MCPM and β-TCP can be selected based on their equimolar, stoichiometric relationship in the brushite-forming reaction. In one embodiment, the MCPM powder is present at a concentration of about 3 to about 7 weight percent, based on the total weight of the particulate composition, and the β-TCP is present in an amount of about 3.72 to about 8.67 weight percent.

It has been discovered that the MCPM and β-TCP powders can react prematurely during storage in the presence of residual moisture to form brushite and/or monetite, an undesirable anhydrous analog of brushite. Thus, storage of the brushite-forming calcium phosphate powders together in a homogenous mixture can result in reduction in the amount of brushite produced upon mixing the particulate composition with the aqueous mixing solution to form the bone graft substitute cement, which in turn, can alter the properties of the bone graft substitute cement in an undesirable manner. As a result, in a preferred embodiment, the two calcium phosphate components are either packaged together in a dry environment and hermetically sealed against moisture invasion during storage or are packaged separately during storage. In one embodiment, the two calcium phosphate powders are packaged separately, wherein each powder is either packaged alone with no other components of the particulate composition of the invention or in admixture with one or more of the remaining components (e.g., the CSH powder).

In certain embodiments, the particulate composition of the invention will also include a plurality of β-TCP granules having a median particle size greater than the median particle size of the β-TCP powder. The β-TCP granules typically have a median particle size of about 75 to about 1,000 microns, more preferably about 100 to about 400 microns, and most preferably about 180 to about 240 microns. The granules serve to further reduce the resorption rate of the bone graft substitute cement and contribute to scaffold formation. The β-TCP granules are typically present at a concentration of up to about 20 weight percent, based on the total weight of the particulate composition, more preferably up to about 15 weight percent based on the total weight of the composition, and most preferably up to about 12 weight percent. In one preferred embodiment, the β-TCP granules are present at a concentration of about 8 to about 12 weight percent. The β-TCP granules can provide a relatively inert third phase in the final cement that exhibits an even slower resorption rate than the brushite formed by reaction of the MCPM and the β-TCP powder. Thus, the presence of the granules can further alter the resorption profile of the resulting bone graft substitute cement.

Both the β-TCP granules and the β-TCP powder used in the present invention can be formed using a commercially available β-TCP powder as a starting material, such as β-TCP powder available from Plasma Biotal Ltd. (Derbyshire, UK). In one embodiment, the β-TCP components of the particulate composition are formed by first wet milling a commercially available β-TCP powder in a ball mill to a median particle size of less than 1.0 micron and then draining the resulting slurry through a strainer to remove the milling media. Thereafter, the solid cake of β-TCP can be separated from any remaining liquid components using any of a variety of techniques known in the art, such as centrifuging, gravity separation, filter pressing, evaporation, and the like. The dry cake is then processed through a series of sieves in order to produce two separate β-TCP components having different median particle sizes. The dried cake of β-TCP is typically milled either during or prior to sieving in order to fragment the cake. In one preferred embodiment, the system of sieves produces a β-TCP component having a particle size range of about 125 to about 355 microns in a green (i.e., unfired) state and another β-TCP component having a particle size range of about 75 to about 355 microns in a green state. Thereafter, the two β-TCP components are sintered, and thereby densified, by heat treatment in a furnace. In one embodiment, the furnace treatment involves heating the β-TCP powder components on an alumina plate at a temperature of about 1100-1200° C. for about three hours. It is typical to ramp the temperature up to the desired sintering temperature and ramp the temperature back down during the cooling period at a rate no greater than about 5-6° C. per minute.

Following the sintering process, the densified β-TCP granules having had a green state particle size of about 125 to about 355 microns can be used as the granule component of the particulate composition. The sintered β-TCP component having had a green (i.e., unfired) state particle size of about 75 to about 355 microns can be dry milled in a ball mill for approximately one to four hours in order to form the β-TCP powder having a median particle size of less than about 20 microns, which can then be used in the particulate composition as described above.

The aqueous component that is mixed with the particulate composition of the invention is selected in order to provide the composition with a desired consistency and hardening or setting time. Typically, the aqueous solution is provided in an amount necessary to achieve a liquid to powder mass ratio (L/P) of at least about 0.2, more preferably at least about 0.21, and most preferably at least about 0.23. A preferred L/P ratio range is about 0.2 to about 0.3, more preferably about 0.2 to about 0.25.

Examples of suitable aqueous components include water (e.g., sterile water) and solutions thereof, optionally including one or more additives selected from the group consisting of sodium chloride, potassium chloride, sodium sulfate, potassium sulfate, EDTA, ammonium sulfate, ammonium acetate, and sodium acetate. In one preferred embodiment, the aqueous mixing solution used is a saline solution or a phosphate buffered saline solution. An exemplary aqueous solution is 0.9% NaCl saline solution available from Baxter International (Deerfield, Ill.) and others.

In one embodiment, the aqueous solution further includes one or more organic or inorganic carboxylic acid-containing compounds (hereinafter carboxylic acids or carboxylic acid compounds) which may or may not contain a hydroxyl group on the alpha carbon, optionally titrated to a neutral pH using a suitable base (e.g., neutralized to a pH of about 6.5 to about 7.5 using an alkali metal base such as sodium hydroxide or potassium hydroxide), which can alter water demand, flowability, and/or viscosity of the bone graft substitute cement composition upon mixing. Exemplary carboxylic acids include glycolic acid and lactic acid. Preferred carboxylic acids have a single carboxylic acid group, from 1 to about 10 total carbon atoms (e.g., 1, 2, 3, 4, 5, 6, 7, 8, 9, or 10 carbon atoms including the carbonyl carbon), and 0-5 hydroxyl groups (e.g., 0, 1, 2, 3, 4, or 5) attached to the carbon chain. In one embodiment, the mixing solution is a 0.6M solution of glycolic acid neutralized to a pH of 7.0 using NaOH. Reference to the carboxylic acid compound herein encompasses both the free acid and salt forms.

It has been discovered, as set forth in Example 3, that the presence of the carboxylic acid component in the aqueous solution prior to gamma radiation sterilization can lead to inconsistent bone graft substitute cement properties, such as "drift" in cement setting time, due to degradation of the acid resulting from the radiation exposure. Thus, in one preferred embodiment, the carboxylic acid compound discussed above in connection with the aqueous mixing solution is packaged as a crystalline powder (e.g., in free acid or salt form) with the remaining particulate components of the kit, either in admixture with one or more other powder components or in a separate container, rather than in solution. Using the acid component in powder form avoids degradation of the acid upon sterilization of the composition with gamma radiation. Alternatively, the carboxylic acid component is added to the aqueous solution after the solution is sterilized by radiation so that the carboxylic acid is not exposed to sterilizing radiation while in solution.

In one embodiment, the carboxylic acid for use in the invention is neutralized to a pH of about 6.5 to about 7.5 in solution using, for example, an alkali metal base as noted above, and then isolated as a crystalline powder by evaporation of the solvent (e.g., water). The crystalline powder is typically isolated in a salt form, such as an alkali metal salt form (e.g., lithium, sodium, or potassium salts). Exemplary dry crystalline powders of a carboxylic acid, in salt form, for use in the invention include sodium glycolate, potassium glycolate, sodium lactate, and potassium lactate. The powdered carboxylic acid salt can be added to any of the other powder ingredients that together form the particulate portion of the bone graft substitute cement, such as the CSH component or either of the calcium phosphate components. However, in certain embodiments, the powdered carboxylic acid is stored in a separate container so that it can be reconstituted with the aqueous solution prior to mixing the solution with the remaining particulate components of the composition.

The bone graft substitute cement of the invention can further include other additives known in the art. The additives can be added as a solid or liquid to either the particulate composition of the invention or the aqueous mixing solution. One example of an additive for the calcium sulfate composition is a plasticizer designed to alter the consistency and setting time of the composition. Such a plasticizing ingredient can retard the setting of calcium sulfate hemihydrate pastes, thereby increasing the time it takes for the composition to set following mixing with an aqueous solution. Exemplary plasticizers include glycerol and other polyols, vinyl alcohol, stearic acid, hyaluronic acid, cellulose derivatives and mixtures thereof. Alkyl celluloses are particularly preferred as the plasticizer ingredient. Exemplary alkyl celluloses include methylhydroxypropylcellulose, methylcellulose, ethylcellulose, hydroxyethylcellulose, hydroxypropylcellulose, hydroxypropylmethylcellulose, carboxymethylcellulose, cellulose acetate butyrate, and mixtures or salts thereof.

Exemplary additives also include biologically active agents. As used herein, the term "biologically active agent" is directed to any agent, drug, compound, composition of matter or mixture that provides some pharmacologic affect that can be demonstrated in vivo or in vitro. Examples of biologically active agents include, but are not limited to, peptides, proteins, enzymes, small molecule drugs, dyes, lipids, nucleosides, oligonucleotides, polynucleotides, nucleic acids, cells, viruses, liposomes, microparticles, and micelles. It includes agents that produce a localized or systemic effect in a patient.

Particularly preferred classes of biologically active agents include osteoinductive or osteoconductive materials, antibiotics, chemotherapeutic agents, pesticides (e.g., antifungal agents and antiparasitic agents), antivirals, anti-inflammatory agents, and analgesics. Exemplary antibiotics include ciprofloxacin, tetracycline, oxytetracycline, chlorotetracycline, cephalosporins, aminoglycosides (e.g., tobramycin, kanamycin, neomycin, erythromycin, vancomycin, gentamycin, and streptomycin), bacitracin, rifampicin, N-dimethylrifampicin, chloromycetin, and derivatives thereof. Exemplary chemotherapeutic agents include cis-platinum, 5-fluorouracil (5-FU), taxol and/or taxotere, Ifosfamide, methotrexate, and doxorubicin hydrochloride. Exemplary analgesics include lidocaine hydrochloride, bipivacaine and non-steroidal anti-inflammatory drugs such as ketorolac tromethamine. Exemplary antivirals include gancyclovir, zidovudine, amantidine, vidarabine, ribaravin, trifluridine, acyclovir, dideoxyuridine, antibodies to viral components or gene products, cytokines, and interleukins. An exemplary antiparasitic agent is pentamidine. Exemplary anti-inflammatory agents include $\alpha$-1-anti-trypsin and $\alpha$-1-antichymotrypsin.

Useful antifungal agents include diflucan, ketaconizole, nystatin, griseofulvin, mycostatin, miconazole and its derivatives as described in U.S. Pat. No. 3,717,655, the entire teachings of which are incorporated herein by reference; bis-diguanides such as chlorhexidine; and more particularly quaternary ammonium compounds such as domiphen bromide, domiphen chloride, domiphen fluoride, benzalkonium chloride, cetyl pyridinium chloride, dequalinium chloride, the cis isomer of 1-(3-chloroallyl)-3,5,7-triaza-1-azoniaadamantane chloride (available commercially from the Dow Chemical Company under the trademark Dowicil 200) and its analogues as described in U.S. Pat. No. 3,228,828, the entire teachings of which are incorporated herein by reference, cetyl trimethyl ammonium bromide as well as benzethonium chloride and methylbenzethonium chloride such as described in U.S. Pat. Nos. 2,170,111; 2,115,250; and 2,229,024, the entire teachings of which are incorporated herein by reference; the carbanilides and salicylanilides such 3,4,4'-trichlorocarbanilide, and 3,4,5-tribromosalicylanilide; the hydroxydiphenyls such as dichlorophene, tetrachlorophene, hexachlorophene, and 2,4,4'-trichloro-2'-hydroxydiphenylether; and organometallic and halogen antiseptics such as sinc pyrithione, silver sulfadiazone, silver uracil, iodine, and the iodophores derived from non-ionic surface active agents such as described in U.S. Pat. Nos. 2,710,277 and 2,977,315, the entire teachings of which are incorporated herein by reference, and from polyvinylpyrrolidone such as described in U.S. Pat. Nos. 2,706,701, 2,826,532 and 2,900,305, the entire teachings of which are incorporated herein by reference.

As used herein, the term "growth factors" encompasses any cellular product that modulates the growth or differentiation of other cells, particularly connective tissue progenitor cells. The growth factors that may be used in accordance with the present invention include, but are not limited to, fibroblast growth factors (e.g., FGF-1, FGF-2, FGF-4); platelet-derived growth factor (PDGF) including PDGF-AB, PDGF-BB and PDGF-AA; bone morphogenic proteins (BMPs) such as any of BMP-1 to BMP-18; osteogenic proteins (e.g., OP-1, OP-2, or OP-3); transforming growth factor-$\alpha$, transforming growth factor-$\beta$ (e.g., ($\beta$1, $\beta$2, or $\beta$3); LIM mineralization proteins (LMPs); osteoid-inducing factor (OIF); angiogenin(s); endothelins; growth differentiation factors (GDF's); ADMP-1; endothelins; hepatocyte growth factor and keratinocyte growth factor; osteogenin (bone morphogenetic protein-3); heparin-binding growth factors (HBGFs) such as HBGF-1 and HBGF-2; the hedgehog family of proteins including indian, sonic, and desert hedgehog; interleukins (IL) including IL-1 thru -6; colony-stimulating factors (CSF) including CSF-1, G-CSF, and GM-CSF; epithelial growth factors (EGFs); and insulin-like growth factors (e.g., IGF-I and -II); demineralized bone matrix (DBM); cytokines; osteopontin; and osteonectin, including any isoforms of the above proteins. Particulate DBM is a preferred osteoinductive additive.

The biologically active agent may also be an antibody. Suitable antibodies, include by way of example, STRO-1, SH-2, SH-3, SH-4, SB-10, SB-20, and antibodies to alkaline phosphatase. Such antibodies are described in Haynesworth et al., Bone (1992), 13:69-80; Bruder, S. et al., Trans Ortho Res Soc (1996), 21:574; Haynesworth, S. E., et al., Bone (1992), 13:69-80; Stewart, K., et al, J Bone Miner Res (1996), 11(Suppl.):S142; Flemming J E, et al., in "Embryonic Human Skin. Developmental Dynamics," 212:119-132, (1998); and Bruder S P, et al., Bone (1997), 21(3): 225-235, the entire teachings of which are incorporated herein by reference.

Other examples of biologically active agents include bone marrow aspirate, platelet concentrate, blood, allograft bone, cancellous bone chips, synthetically derived or naturally derived chips of minerals such as calcium phosphate or calcium carbonate, mesenchymal stem cells, and chunks, shards, and/or pellets of calcium sulfate.

A bone graft substitute cement according to the invention can be formed by mixing the particulate composition with the aqueous solution using manual or mechanical mixing techniques and apparatus known in the art. It is preferred to mix the components of the cement at atmospheric pressure or below (e.g., under vacuum) and at a temperature that will not result in freezing of the aqueous component of the mixture or significant evaporation. Following mixing, the homogenous composition typically has a paste-like consistency, although the viscosity and flowability of the mixture can vary depending on the additives therein. The bone graft substitute cement material can be transferred to a delivery device, such as a syringe, and injected into a target site, for example, to fill in cracks or voids of a bone defect. In some embodiments, the material can be injected through an 11 to 16-gauge needle up to, for example, 10 cm long.

The bone graft substitute cements of the invention will generally set, as defined by the Vicat needle drop test set forth below, in about 3 to about 25 minutes, more preferably about 10 to about 20 minutes. The bone graft substitute cement material of the invention will typically reach a hardness comparable to or greater than bone within about 30 to about 60 minutes. Setting of the material can occur in a variety of environments, including air, water, in vivo, and under any number of in vitro conditions.

The hardened bone graft substitute cement preferably exhibits certain mechanical strength properties, particularly as characterized by diametral tensile strength and compressive strength. Preferred embodiments of the cement exhibit a diametral tensile strength of at least about 4 MPa after curing for one hour in ambient air following mixing of the particulate composition with an aqueous solution, more preferably a diametral tensile strength of at least about 5 MPa, most preferably at least about 6 MPa. Further, preferred embodiments of the bone graft substitute cement exhibit a diametral tensile strength of at least about 8 MPa after curing for 24 hours in ambient air following mixing of the particulate composition with an aqueous solution, more preferably a diametral tensile strength of at least about 9 MPa after curing for 24 hours, and most preferably at least about 10 MPa.

Preferred embodiments of the bone graft substitute cement also exhibit a high level of compressive strength, such as a compressive strength of at least about 15 MPa after curing for one hour in ambient air following mixing of the particulate composition with an aqueous solution, more preferably a compressive strength of at least about 40 MPa. Further, preferred embodiments of the bone graft substitute cement will exhibit a compressive strength of at least about 50 MPa after curing for 24 hours in ambient air following mixing of the particulate composition with an aqueous solution, more preferably a compressive strength of at least about 80 MPa.

The bone graft substitute cement of the invention will also exhibit a dissolution rate that is significantly slower than a comparable bone graft substitute cement made substantially entirely of calcium sulfate. In certain preferred embodiments, the cement of the invention exhibits an average dissolution rate, expressed as an average percentage of weight loss per day, that is at least about 25% lower than the average dissolution rate of a cement formed using a particulate composition consisting of calcium sulfate, the average dissolution rate measured by immersion of a 4.8 mm OD pellet having a length of 3.3 mm in distilled water at 37° C. as described in greater detail below. More preferably, the bone graft substitute cement of the invention has an average dissolution rate that is at least about 30% lower than a calcium sulfate cement, most preferably at least about 35% lower, and in some embodiments, as much as 40% lower or more. A preferred range of dissolution, expressed as an average percentage of weight loss per day measured using the test procedure set forth below, is about 5% to about 15%, more preferably about 7% to about 13%. Average dissolution rates stated are determined by linear regression of % weight loss per day using data from days 0, 1, 2, 3, and 4 determined using the procedure set forth below.

The present invention also provides a bone graft substitute kit comprising the particulate composition of the invention. Typically, the kit comprises one or more containers enclosing the particulate composition as described above and a separate container enclosing a sterile aqueous solution. The kit will typically contain a written instruction set describing a method of using the kit. In addition, the bone-graft substitute kit of the invention will preferably comprise an apparatus for mixing the particulate composition with the aqueous solution in order to form the bone graft cement, such as a vacuum mixing apparatus. Additionally, the kit will typically include a device for delivering the bone graft cement to the site of the bone defect, such as an injection device (e.g., a needle and syringe).

The particular composition and the sterile aqueous solution will typically be sterilized by irradiation prior to packaging in the kit.

As noted previously, in certain embodiments, the kit of the invention will separate the two calcium phosphate powder components into different containers to avoid reaction during storage. There are a number of packaging configurations that can accomplish this goal. For example, in one embodiment, the kit includes one container for CSH powder, one container for β-TCP powder, and one container for MCPM powder. In another embodiment, the kit includes two containers for the particulate composition, one including β-TCP powder and a portion of the CSH component and a second containing MCPM powder and a portion of the CSH component. In yet another embodiment, the MCPM powder is packaged in a separate container by itself, and the β-TCP powder and the CSH powder are packaged together. In a still further embodiment, the β-TCP powder is packaged in a separate container by itself, and the MCPM powder and the CSH powder are packaged together. In any of the above embodiments, any of the powder containers can further include the crystalline powder of the carboxylic acid salt component and/or the β-TCP granules, or those components could be packaged separately in their own containers. When present, the accelerator adapted to accelerate conversion of CSH to CSD is typically in admixture with the CSH powder. In one preferred embodiment, the kit comprises one container enclosing the MCPM powder, and a second container enclosing the remaining particulate ingredients in admixture, such as one or more of the CSH powder, the CSH accelerator, the β-TCP powder, the β-TCP granules, and the carboxylic acid crystalline powder.

In one preferred embodiment, the powdered form of the carboxylic acid is packaged separately so that it can be reconstituted in the aqueous solution, if desired, prior to mixing the solution with the remaining particulate components. However, as noted previously, the aqueous solution of the kit may also contain the carboxylic acid component in solution form if the carboxylic acid is added after radiation sterilization of the aqueous component of the kit.

It can be important to utilize all of the aqueous solution packaged in the kit in order to ensure that consistent setting times are achieved. In one embodiment, the aqueous solution is packaged in a highly hydrophobic container, such as a glass syringe or other glass container, that is less prone to retention of residual solution in amounts that will cause changes in the performance characteristics of the bone graft substitute cement.

The present invention also provides a method for treating a bone defect. The method of the invention involves applying a bone graft substitute cement as described above to the site of the bone defect. The bone graft substitute cement can be applied in flowable form following mixing of the particulate composition with the aqueous solution, such as through an injection device, prior to setting of the composition. Alternatively, the bone graft substitute cement can be used in a precast hardened form, wherein the cement is provided in predetermined shapes such as pellets, granules, wedges, blocks, or disks, or used in the form of randomly-shaped shards created by mechanically breaking a cement mass into smaller pieces. In a further embodiment, the clinician can form the bone graft cement mixture and manually mold the mixture into a desired shape, such as the shape needed to fill a particular bone defect, prior to application.

In another embodiment, the bone graft substitute cement of the invention can be incorporated into an orthopedic implant, such as any of the various devices adapted for joint replacement. The bone graft substitute cement is typically incorporated into such devices as an outer coating or as a filling material within the pores of a porous outer component of the device. In this embodiment, the bone graft substitute cement facilitates bone ingrowth in the area surrounding the implanted device. Exemplary orthopedic implants include knee replacement devices (e.g., constrained or non-constrained knee implant devices, hinged knee devices, metallic plateau knee devices, and patellar devices), hip replacement devices (e.g., acetabular components and femoral components), elbow replacement devices (e.g., constrained, semi-constrained, and non-constrained devices), upper femoral devices, upper humeral devices, wrist replacement devices (e.g., semi-constrained 2- and 3-part articulation devices), shoulder devices, passive tendon devices, spinal devices (e.g., thoracolumbar spinal fixation devices, cervical spinal fixation devices, and spinal fusion cages), finger/toe devices, and diaphysis devices.

The present invention will be further illustrated by the following non-limiting example.

EXPERIMENTAL

Example 1 illustrates in vivo use of a bone graft substitute cement of the invention, and particularly describes the reduced resorption rate (as compared to a calcium sulfate composition), good mechanical properties, and acceptable setting times exhibited by the inventive composition. Example 2 illustrates the ability of an embodiment of the inventive composition increase the amount, strength, and stiffness of restored bone as compared to use of conventional $CaSO_4$ pellets. Example 3 demonstrates the degradation effect of gamma radiation on glycolic acid in solution, and the effect of such degradation on setting times of the bone graft substitute cement. Example 4 demonstrates that placement of a glycolic acid salt form in the particulate composition reduces the effect of radiation on the performance of the bone graft substitute cement without sacrificing other advantageous properties, such as certain handling and mechanical strength properties.

Setting Time Measurement

Setting times can be measured using a Vicat needle that is 1 mm in diameter, 5 cm long, and which possesses a total weight of 300 g, all per ASTM C-472, which is incorporated by reference herein in its entirety. The sample being tested should be mixed in a manner that a homogeneous, flowable paste is created. The sample size for the Vicat needle drop test is about 3 cc to about 5 cc of material tapped down to a cake in an approximately 20 mL polyethylene cup; the sample shall be handled such that no agitation is inflicted upon the material 1 minute after the aqueous solution contacts the particulate composition other than the dropping and removal of the Vicat needle. The cup should be of such dimensions that the cake is a short, flat cylinder measuring about ¼" to about ⅜" in height.

Set time according to the Vicat needle drop test is defined as the amount of time elapsed between the time the aqueous solution contacts the particulate composition and the time the Vicat needle will not pass through 50% of the height of a cement sample upon being dropped from the upper surface of the sample. The needle is allowed to fall under its own weight, under gravity alone, through a line perpendicular to the top and bottom, flat faces of the cylinder-shaped sample cake. The needle is dropped every 30 seconds after the first drop. The needle shall not be dropped more than 6 times during the duration of the test. If after the $6^{th}$ drop the needle continues to pass through more that 50% of the height of the sample, the test must be repeated with fresh material; a new, clean cup; and a clean Vicat needle free of debris, especially that which is left behind from previous tests. Cups, mixing equipment, and material transfer equipment should not be reused. All materials and equipment used during testing should be between 21-27° C. and exposed to an environment with a relative humidity between 20-50%.

Compression Strength Measurement

Compression strength of the material is determined through the following test methodology. Specimens are cast to size per ASTM F451 (6 mm outer diameter×12 mm in length), which is incorporated by reference in its entirety, utilizing a stainless steel split mold with a capacity of eight specimens.

The split mold is placed on a glass plate with the cylindrical voids, specimen slots, standing upright. The material is mixed and then loaded into a device for delivery of the material into the slots such that a back filling method can be utilized; a syringe with a jamshidi-type needle is commonly used. Each specimen slot is filled from bottom to top in a back filling manner. It is customary to excessively fill the mold such that excess material extrudes out above the dimensions of the split molds, this assures displacement of any air entrapped within the specimen slots. It may be necessary to hold mold down on to glass plate during casting to prevent material from extruding out of the bottom of the specimen slots, between the glass plate and mold.

Upon filling each specimen slot another glass plate is pushed by hand onto the excess material located on the top of the mold, producing a thin sheet of flashing across the tops of the specimens and split mold itself. This glass plate is of a size which does not produce an excessive compressive force or a pressurized environment in which the material cures. All specimens are cast and flashing is created within 2 minutes of the aqueous solution coming into contact with the particulate component.

The specimens are demolded 30 minutes after the aqueous solution has come into contact with the particulate component. First the flashing is removed from both sides of the split mold containing the faces of the specimens; regardless of holding mold against the lower glass plate upon casting, a thin film of flashing is created on the lower surface of the mold. Commonly, a razor blade is used to scrape off the flashing and in doing so create smooth faces on the specimens. The split mold is separated and the specimens are removed. All specimens should be removed within 32 minutes of the aqueous solution coming into contact of the particulate component. Upon removal of the specimens, they should be allowed to continue curing in air at room condition (21-27° C.; 20-50% relative humidity) until time of testing.

Testing of the material is performed at a predetermined time after the aqueous solution has come into contact with the particulate component. Commonly, testing is performed at 1 hr and 24 hrs. Testing is performed on a compression test fixture per ASTM D695, which is incorporated by reference herein in its entirety. The compression test fixture is placed on a mechanical test frame capable of displacement control and monitoring of displacement and force through data acquisition running at 50 Hz or faster.

The specimens are tested individually on the compression test frame. The specimens are placed between the platens in a manner such that the cylinder faces are positioned against the platens. The compression test frame containing the specimen is loaded in compression at a rate of 0.333 mm/sec until failure. Force and displacement are monitored throughout the test, and maximum force at failure is noted. Proper failure will result in a fracture across the height of the specimen. The maximum compression force at failure is noted. Failure is defined as a sudden drop in load, deviation of the loading curve from the initial slope created by the loading of the specimen, and/or the force noted upon visual failure of the specimen.

The compression strength in MPa is then calculated as followed: $(Pmax)/(\pi * R^2)$; where Pmax is the load at failure in Newtons, $\pi$ is approximately 3.14, and R is the radius of the specimen in mm (3).

It is crucial when performing compression strength specimen preparation that all equipment used is clean of all debris, especially that of the cured material of interest.

Diametral Tensile Strength Measurement

The diametral tensile strength is determined through the following test methodology. A 1" cube of 10 lb/ft$^3$ closed-cell polyurethane foam (available as Last-A-Foam® from General Plastics Manufacturing Company, Tacoma, Wash.) with an approximately ⅝ in. (15.8 mm) outer diameter cylindrical void and notches for side removal is used as the specimen mold. The approximately ⅝ in. outer diameter cylindrical void is created by drilling perpendicularly through opposite faces of the cube in one depression of a drill press utilizing a ⅝ in. drill bit. The void runs the entire length of the cube and is centered such that both opposite, drilled faces share the same center as the circular voids created in them from the drilling. Two opposite sides from the remaining four full sides are designated to become the open sides of the final specimen; these sides will be removed via the notches. These sides are notched, two notches per side, in a manner such that they can be removed immediately prior to testing and not affect the sample integrity. The notches shall run the entire length of the cube and be separated in a manner that upon removal >50% of the height of the specimen is exposed. Commonly the notches are created using an upright band saw. FIGS. 2a-2c illustrate an exemplary diametral tensile test mold 20. FIG. 2a provides a top and bottom view of the mold 20. FIG. 2b provides a side view of the mold 20. FIG. 2c provides a front and rear view of the mold 20 and shows a 16 mm outer diameter cylindrical void 30 therein.

The material to be tested is mixed to a homogeneous paste and loaded into a device suitable for injection of the paste into the 16 mm outer diameter cylindrical void. Commonly a 30 cc syringe with a 1 cm opening is used for this. The mold is held by hand using the thumb and middle finger positioned on the opposite, notched sides. The index finger of the hand used to hold the mold is positioned over one of the circular openings. The material is then injected into the void from the opposite side of the void from the index finger; the entire face of the syringe exhibiting the 1 cm opening is lightly pushed up against the circular opening of the mold. Upon injection of the material into the mold, pressure will be felt on the index finger covering the back opening from the ejected material. The index finger is slowly removed while filling continues, allowing the paste to flow out of the rear of the mold in an extrusion with the same 16 mm outer diameter as the void. The syringe is slowly backed out from the front opening while back filling of paste is performed through further ejection from the syringe until the entire void is filled and excess material is located outside the dimensions of the original cube of foam. The front and rear sides of the specimen are wiped smooth, flush with the front and rear sides of the mold using a spatula. All specimens to be tested should be made within 2 minutes from the start of mixing, defined by the aqueous solution coming into contact with the particulate composition.

The specimens are allowed to cure horizontally in air in the mold with the front and rear sides of the mold exposed to air at room conditions (21-27° C.; 20-50% relative humidity) for a predetermined amount of time, normally 1 hr or 24 hrs. This predetermined amount of time begins at the time at which the aqueous solution comes into contact with the particulate composition at the beginning of the mixing process.

Testing is performed on a mechanical test frame capable of displacement control and of monitoring displacement and force through data acquisition running at 20 Hz or faster. The sides of the specimen mold are removed immediately prior to testing; only the areas between the notches are removed.

Removal of the sides is normally performed with a knife. The top and bottom of the mold are held between two fingers with slight pressure to prevent specimen surface-to-mold interface damage. The knife blade is placed into one of the notches and then twisted to break the area between the notches free; this is repeated for the other side in the same manner. The tops and bottom of the molds are left in place to hold the specimen and prevent shear stresses on the surface. The specimen is placed between two flat, parallel platens; one of which is free to swivel to allow alignment with the loading train. The swiveling platen assures an equally distributed load across the specimen contact points. The specimen is loaded transversely at a rate of 5 mm/minute until failure. Proper failure will result in a vertical fracture completely through the length of the specimen. The maximum force at failure is noted.

A loading curve of force versus displacement is created to determine the maximum force at failure, in which displacement and force are positive values. The first part of the loading curve shows the loading of the foam followed by its compression. The compression of the foam portion will be evident by continued displacement with no substantial increase in force; this can also be seen visually during the test. After the foam is completely compressed, the force will begin to rise again, creating an increasing slope on the loading curve followed by a constant slope as the load is transferred to the specimen. The increasing slope is commonly known as a "toe in". Failure is defined as a sudden drop in load, a decrease in the slope of the loading curve after the constant slope from specimen loading has been established, and/or the force noted upon visual failure of the specimen while the test is running.

The diametral tensile strength in MPa is then calculated as followed: $(2*Pmax)/(\pi * L * H)$; where Pmax is the load at failure in Newtons, $\pi$ is approximately equal to 3.14, L is the length of the specimen in mm (25.4), and H is the height of the specimen in mm (16). Specimens are disqualified for diametral tensile strengths if any one or more of the following occur: fracture is not vertical, facture does not completely run the length of the specimen, length of the specimen fails, or voids in the material are seen on the fractured walls of the specimen.

It is crucial when performing diametral tensile strength specimen preparation that all equipment used is clean of all debris, especially that of the cured material of interest.

Dissolution Rate Measurement

Dissolution rate of the material is determined through the following methodology. Specimens are cast in silicone molds to a size of 4.8 mm outer diameter and 3.3 mm tall cylinders. A 3.3 mm thick sheet of silicone containing cylindrical voids is used as a mold. Cylindrical voids are 4.8 mm in outer diameter and 3.3 mm tall, and orientated such that the circular faces of the void are parallel and in the same plane as the surfaces of the silicone sheet.

A thin sheet of polyethylene is laid on a table. A polyethylene mesh is placed on top of the polyethylene sheet; sheet and mesh are of same dimensions (excluding thickness) and positioned such that the mesh masks the sheet from the top. Next a silicone mold of smaller dimensions is placed on top of the mesh (excluding thickness). No part of the mold hangs off the edge of the mesh or sheet.

The material to be tested is then mixed together to form a homogeneous paste. The paste is then wiped across the top of the mold using a spatula in a manner that the voids are packed with the material. The mesh will allow air to be displaced out of the void as the mold is filled. Several wipes are performed to assure that material has completely penetrated to bottom of the mold and extruded out through the mesh and onto the lower polyethylene sheet. A final wipe with the spatula across the top of the mold is performed to remove the majority of excess material and produce smooth top faces for the specimens.

Another polyethylene sheet of the same dimensions of the as the first is then placed across the top of the mold, such that it completely covers the top of the mold. This sheet is then gently pressed against the mold using a finger in a gentle rubbing motion. An intimate contact between the top polyethylene sheet and the specimens is created.

The entire system, sheet, mesh, mold, and sheet, is then picked up as a whole and flipped over in a manner such that the original top is now facing down. The system is held by hand and slapped repeatedly onto table in a manner such that any air entrapped in the molds will be displaced out by the material; slapping of the system should not be excessive in force or repetitions. Upon removal of the majority of the air the system is returned to table in the upside down orientation, sheet and mesh side up. The top polyethylene sheet, originally the bottom, and mesh are removed and the spatula is again used to wipe material into voids in the tops (previously bottoms) of the specimens created from air removal. A final wipe with the spatula across the top of the mold is performed to remove the majority of excess material. The sheet (no mesh) is returned to the top of the mold. The sheet is then pressed against the mold using a finger in a gentle rubbing motion. An intimate contact between the top and bottom polyethylene sheet and the specimens has now been created.

The specimens are left in the mold to cure for a minimum of 8 hrs after the second polyethylene sheet has been placed in direct contact with the specimens and mold (no mesh). After at least 8 hrs have passed, the specimens are demolded by hand. Any flash remaining attached to pellet faces are removed by rolling specimen between fingers. All defective specimens are disqualified from the test and discarded. A defective specimen is defined as a specimen not exhibiting a cylindrical shape, which could be caused by entrapped air, defects created upon demolding, and/or physical damage to the specimen itself.

All specimens which are not defective are spread across a stainless steel pan in a monolayer. The pan and specimens are then dried in an oven at 40° C. for a minimum of 4 hrs, and then removed from oven and allowed to cool for 30 minutes in room conditions (21-27° C.; 20-50% relative humidity).

From the specimens created, five (5) specimens are arbitrarily chosen to be used for dissolution testing. Each specimen chosen is paired with a clean cylindrical fritted glass extraction thimble of the following dimensions: 90.25 mm overall height, 4 mm fitted glass base (40-60 micron pores) located 80 mm from top of thimble, 25 mm outer diameter, and 22 mm inner diameter. The mass of each extraction thimble is measured (0.01 mg) and noted. The mass of each specimen in measured (0.01 mg) and noted. A polyethylene bottle (300 mL) is designated to each pair (specimen and thimble). The bottle has dimensions that allow thimble and specimen to easily be placed in and removed from bottle and upon filling with 275 mL of water will create a column of water that is taller than the thimble. The bottle is filled with 275 mL of distilled water at room temperature (21-27° C.). The specimen is placed into its corresponding thimble and the thimble is lowered into the bottle; care is taken to keep any part of the material from escaping from the thimble. The bottle is capped and placed into a water bath at 37° C. with no agitation and the time is noted.

24 hrs after the specimen has been in the water, the thimble containing the specimen is retrieved. The water is allowed to drain out of the thimble through the fritted glass base. The thimble containing the specimen is then dried for 4 hrs in a 40° C. oven or until completely dried (determined gravimetrically). The thimble containing the specimen is then allowed to cool down for 30 minutes at room conditions (21-27° C.; 20-50% relative humidity).

The thimble-containing the pellet is then weighed to an accuracy of 0.01 mg. Subtracting the known empty thimble mass from the mass of the combination will result in the mass of the specimen alone. Subtracting this mass from the initial specimen mass will produce the mass lost to dissolution. This mass lost can be divided by the specimen initial mass and the product of that multiplied by 100 will result in the % mass lost from dissolution.

At this point the thimble containing the pellet is returned to the bottle containing fresh distilled water (275 mL) at room temperature (21-27° C.), and the bottle is capped and returned to the water bath. After 24 hrs the drying and weighing process is repeated. These actions are repeated with fresh distilled water after every 24 hr soak until the test is terminated or the material completely dissolves.

Example 1

Diametral tensile strength, dissolution properties, and in vivo evaluation of new bone ingrowth and residual material of bone graft cements of the invention were compared to a commercially available calcium sulfate material. The experimental group for all experiments was an embodiment of the current invention including a cement consisting of 74.906 weight percent calcium sulfate hemihydrate, 0.094 weight percent accelerator (sucrose coated calcium sulfate dihydrate), 6.7 weight percent monocalcium phosphate monohydrate, 8.3 weight percent beta tricalcium phosphate powder, 10 weight percent beta tricalcium phosphate granules, and an aqueous solution of 0.6 molar glycolic acid neutralized to a pH of 7.00 with 10 normal sodium hydroxide solution (hereinafter "SR"). MIIG® X3 Bone Graft Substitute (hereinafter "X3") (Wright Medical, Arlington, Tenn.) calcium sulfate was used as a control for all experiments. The SR material was formulated to set in 14-19 minutes, whereas the X3 material was formulated to set in 7-10 minutes.

An intermediate resorbing calcium sulfate, calcium phosphate composite cement was also evaluated in this study. Dissolution properties, compression strength, and in vivo evaluation of new bone ingrowth and residual material were evaluated for this material. This material is also an embodiment of the present invention and comprised 84.999 weight percent calcium sulfate hemihydrate, 6.7 weight percent monocalcium phosphate monohydrate, 8.3 weight percent beta tricalcium phosphate powder, 0.0013 weight percent accelerator (sucrose coated calcium sulfate dihydrate), and an aqueous component of water. This intermediate material was formulated to set in 11-16 minutes.

Compression strength was measured on vacuum mixed specimens cast in the manner set forth above. Specimens (n=6) were cured for 1 hr in ambient air. Specimens (n=3) were cured for 24 hrs in ambient air. The specimens were loaded lengthwise using a MTS 858 Bionix test system at a constant rate of 0.333 mm/sec. The compression strength in MPa was calculated using the formula $(Pmax)/(\pi*R^2)$.

Diametral tensile strength (DTS) was measured on vacuum mixed specimens cast in the manner set forth above. The sides of the foam blocks were removed prior to testing. Specimens (n=4) were cured for 1 and 24 hrs in ambient air at room temperature. The specimens were transversely loaded to failure in compression using a MTS 858 Bionix test system at a constant rate of 5 mm/min DTS was calculated from the formula DTS=$(2*P_{max})/(\pi*L*H)$.

Dissolution tests were performed on 4.8 mm OD×3.3 mm cylindrical pellets (n=5). Specimens were placed in 275 mL of distilled water at 37° C. Solutions were changed daily. Specimens were dried and weighed daily for first 30 days and every 5 days thereafter until a residual mass of <5% was achieved. X-Ray diffraction (XRD) was used to identify the residual material.

Results:

FIG. 3 shows the DTS results. One-way ANOVA were performed using JMP software (SAS, Cary, N.C.). A significant difference was seen between 1 and 24 hr cure times for SR cured in air (p<0.001) and no difference for the X3 (p=0.508). It is apparent from the air cured data that the SR reaction is incomplete at 1 hr while the X3 setting reaction is essentially complete. This result was expected based on the differences in setting time.

Average, maximum, and minimum compression strength values for the intermediate material were determined. The 1 hr cure time data produced an average strength of 19.4 MPa, a minimum of 16.2 MPa, and a maximum of 21.4 MPa. The 24 hr cure data produced an average strength of 69.9 MPa, a minimum of 61.4 MPa, and a maximum of 77.3 MPa.

Dissolution results are shown in FIG. 4. Linear regression of days 0 through 4 of the curves were used to estimate the dissolution rates. The average SR rate was 10.7%/day, while the X3 rate was 17.8%/day. The average rate for the intermediate material was 13.5%/day. Following dissolution of 95% of the bone graft substitute cement material, XRD of residual SR material showed it to be beta tricalcium phosphate, a known bioresorbable and osteoconductive material.

A 6-week in vivo pilot study was conducted under an Institutional Animal Care and Use Committee (IACUC) approved protocol. In each of 3 dogs, two defects measuring 9 mm×15 mm were created in each proximal humerus. Each site was filled with either an injected bolus of SR (1-1.5 cc), 4.8 mm OD×3.3 mm pellets of SR, 4.8 mm OD×3.3 mm pellets of X3, or an injected bolus of the intermediate resorbing calcium sulfate, calcium phosphate composite cement. Implants were sterilized with gamma radiation. Each dog received one implant of each material. Healing of the defects and resorption of the pellets and boluses were assessed from radiographs obtained after 0, 2, and 4 weeks and contact radiographs after 6 weeks. New bone formation and residual implanted material in the defects were evaluated using light microscopy of undecalcified, plastic embedded histological sections stained with basic fuchsin and toluidine blue. Area fraction of new bone and residual material in the defects were determined using histomorphometry.

In the in vivo study, the radiographic and histologic data indicated that both types of pellets and boluses were replaced with newly formed osteoid, woven, and lamellar bone that had formed in concentric lamellae at the previous implant sites. At 6 weeks, area fraction of new bone formation was 35.9±6.1% for defects implanted with SR pellets and 26.7±10.0% for defects implanted with X3 pellets. At 6 weeks, the majority of the implanted pellet materials had resorbed, but there was slightly more residual implant material in SR pellet defects compared to the X3 pellet defects. For the SR bolus implants new bone formation was 15.6±5.6% with 29.9±11.9% residual implant material. For the bolus of intermediate resorbing calcium sulfate, calcium phosphate composite cement, new bone formation was 23.4±7.1% with 19.3±8.0% residual implant material. Smaller fractions of new bone formation can be expected for bolus materials at early time due to larger percentages of residual material and smaller surface area to implant volume ratios when compared to that of pellets.

The composite cement of the invention demonstrated consistent setting and strength characteristics similar to those of the control. The goal of slowing down the dissolution rate was achieved, and the early in vivo bone growth was equivalent or superior to the pure calcium sulfate control.

Example 2

Materials and Method:

Under an IACUC-approved protocol, 10 skeletally mature, male dogs (25-32 kgs) had a critical-size, axial medullary defect (13 mm dia×50 mm) created bilaterally in the proximal humerus and were studied for 13 (n=5) and 26 (n=5) weeks. The defect in one humerus was injected with 6 cc of the test material (SR cement according to Example 1). An identical defect in the contralateral humerus received an equal volume of $CaSO_4$ pellets (OSEOSET® pellets, Wright Medical). Radiographs were obtained at 0, 2, 6, 13 and 26 weeks. Transverse, undecalcified stained sections of the bones were prepared. The area fractions of new bone and implanted residual materials in the defects were quantified using standard point-counting techniques. The sections were also examined using high-resolution contact radiographs. The yield strength and modulus of an 8 mm dia.×20 mm test cylinder cored from the midlevel of each defect was determined in unconfined, uniaxial compression tests at a crosshead speed of 0.5 mm/min. The histomorphometric and biomechanical data were analyzed using the Friedman and Mann-Whitney tests. Data are presented as the mean and standard deviation.

Results:

The clinical and postmortem radiographs revealed markedly different rates of resorption of the bone graft substitutes and replacement with bone in the defects. Resorption of the $CaSO_4$ pellets was apparent beginning at 2 weeks and substantially complete by 6 weeks. There was slower resorption of the SR cement, also beginning at 2 weeks, but some cement persisted at 26 weeks.

In all of the stained histological sections, there was restoration of the defects by bone and marrow with only focal areas of fibrous tissue and relatively low volumes of residual implanted material. The area fraction of new mineralized bone at 13 weeks was 2-fold greater in defects treated with SR cement (39.4±4.7%) compared to defects treated with conventional $CaSO_4$ pellets (17.3±4.3%) (p=0.025). At 26 weeks, the bone had remodeled to a more normal architecture, but there was still more bone in defects treated with cement (18.0±3.4%) compared to pellets (11.2±2.6%) (p=0.025).

Residual matrix and β-TCP granules were incorporated into bone trabeculae. Surfaces of the materials not covered by bone appeared to be undergoing remodeling by osteoclast-like cells, some of which contained minute particles. The area fraction of residual matrix was greater in the cement-treated defects at 13 weeks (2.9±2.8%) and at 26 weeks (0.6±0.8%) compared to pellet-treated defects (0.0% at 13 and 26 weeks) (p=0.025 and 0.083, respectively). Residual matrix decreased with time in the cement-treated defects (p=0.047). The area fraction of residual β-TCP granules also decreased from 13 weeks (3.6±1.0%) to 26 weeks (0.8±1.4%) (p=0.016). The maximum dimension of the β-TCP granules decreased from 348±13 μm at 13 weeks to 296±29 μm at 26 weeks (p=0.008).

Cored bone samples from defects treated with the cement were considerably stronger and stiffer than those treated with $CaSO_4$ pellets at both 13 and 26 weeks (Table 1 below). For comparison, similar cored trabecular bone specimens from 8 normal proximal humeri had a yield strength of 1.4±0.66 MPa and a modulus of 117±72 MPa.

TABLE 1

|  | Time (wks) | SR Cement | $CaSO_4$ Pellets |
|---|---|---|---|
| Yield Strength (MPa) | 13 | 5.3 (2.6)* | .90 (.44) |
| Yield Strength (MPa) | 26 | 2.2 (.41)** | .47 (.46) |
| Modulus (MPa) | 13 | 283 (217) | 40.8 (35.6) |
| Modulus (MPa) | 26 | 150 (73)* | 15.8 (23.6) |

*p = 0.025,
**p = .046, different from pellets

Conclusion:

Several Ca-based materials with different resorption rates were successfully combined to produce a cement with a tailored, slower resorption profile. In this cement, the majority of the calcium sulfate and dicalcium phosphate dihydrate matrix resorbs early, promoting bone formation deep into the bolus of cement, while the distributed β-TCP granules provide a scaffold, incorporate into new bone, and are then more slowly resorbed. The engineered cement increased the amount, strength and stiffness of restored bone when compared to conventional $CaSO_4$ pellets after 13 and 26 weeks. This cement holds promise for clinical applications where a strong, injectable and highly biocompatible bone graft substitute would be advantageous.

Example 3

Materials and Method:

250 mL of mixing solution, 0.6M glycolic acid neutralized with sodium hydroxide, was created and the pH was noted with a calibrated pH meter. The solution was made using crystalline glycolic acid (Alfa Aesar Part # A12511; Ward Hill, Mass.), 10N sodium hydroxide solution (EMD Chemicals Part # SX0607N-6; Darmstadt, Germany), and USP water for irrigation (Baxter Healthcare Corporation Part # 2F7112; Deerfield, Ill.).

The solution was then divided into two ~125 mL aliquots and then individually rebottled. One of the bottles was sent out for bulk gamma radiation sterilization, 25-32 kGy dose, and the other was retained as an unsterilized control. Upon return of the sterilized solution the pH of both the sterilized and the non-sterilized solutions were checked with a calibrated pH meter and noted.

A single lot of SR powder of the type utilized in Example 1 was used in this study to avoid lot-to-lot variability in set time and injection forces.

Three vials were filled with 6.9 mL of the unsterilized solution and coupled with three vials of unsterilized SR powder containing 30 g per vial. This group served as a control.

Another group was made to represent the option of aseptic filling of the individual units of neutralized glycolic acid. This group consisted of three vials of 6.9 mL of glycolic acid filled out of the 125 mL of bulk sterilized solution and three vials of SR powder filled to 30 g. The powder vials were sent out for gamma radiation sterilization. This represents sterilization of the bulk solution followed by aseptic filling and coupling in a kit containing the already sterilized unit of powder.

The third and final group represents a preferred manufacturing situation: gamma radiation sterilization of the bulk solution followed by gamma radiation sterilization of the individual units. Three vials of solution were filled to 6.9 mL with the sterilized bulk solution. Another three vials were filled with 30 g of the SR powder. All six of these vials were sent out to sterilization. This represents filling the solution from a bulk sterilized solution, packaging kits containing unsterilized powder with bulk sterilized solution, and then sending the kit out for a final sterilization.

Upon return of all the groups the following testing was performed. All solutions, including the remainder of the bulk solution were checked for pH with a calibrated pH meter and noted. The nine sets of units (three units of unsterilized solution and unsterilized powder, three units of one time bulk sterilized solution and unit sterilized powder, and three units of two times sterilized solution (once in bulk followed by once as a unit) and one time unit sterilized powder) were mixed to form a homogeneous paste under vacuum. Set times of approx. ¼ in. thick aliquot of paste in a 25 mL plastic cup were determined through the use of a 300 g Vicat needle. Injection force from a 3 cc syringe attached to a 6 cm 11 gauge non-tapered, ported jamshidi type needle was determined at 3 and 5 minutes after the powder and solutions had come into contact with one another. Injection forces are reported as forces seen at 15 mm of plunger displacement being displaced at 4.4 mm/sec. Injection testing was performed using a materials test frame in displacement control, and data acquisition was taken at 50 Hz of force and displacement.

Results:

pH drift was seen for all solutions. Results were consistent within a group although the two time sterilized solution produced a pH different from that of the control and one time sterilized group. Specifically, the two times sterilized solution produced an average pH of about 6.3, while the other solution groups exhibited a pH of about 5.5.

Forces of injection for all groups were the same. At the 3 minute time point the injection force was about 25 N, and for the 5 minute time point the injection force was about 40 N.

The set time for the unsterilized and one time sterilized group were consistently around 18.5 minutes, except for one unit of the one time sterilized group which was at 19.75 minutes. Set time measurements for the two times solution sterilized group and one time powder sterilized had consistently shifted to about 22 minutes.

Conclusion:

The pH and set time shifts in the two times sterilized solution group shows degradation of the neutralized glycolic acid solution through gamma radiation sterilization. Although the effects were not pronounced in the one-time sterilized solution, degradation must have occurred in that group as radiation degradation is an additive process.

Example 4

Materials and Method:

First, the effect of gamma sterilization of crystalline glycolic acid (GA) on the material's acid-base titration curve using a stock solution of 0.6M sodium hydroxide (NaOH) was examined. Then, physical property comparisons were made between radiation sterilized samples of a cement powder with solid sodium glycolate (Na-GA) blended into the precursor powder and a non-irradiated material. Diametral tensile strength, injection force, Vicat set time, and morphological (SEM) comparisons of the set cements from each configuration were made. Additionally, Vicat set time comparisons were made between unsterilized samples of each product configuration.

Approximately 50 g of GA (GLYPURE®) available from Dupont) was subjected to gamma radiation sterilization (25-32 kGy dosage). Two ~1M solutions of GA were created at equal volumes, one with the gamma irradiated GA and the other with non-irradiated GA of the same manufacturing lot. In order to avoid loss of material during liquid transfers and from evaporation, the solutions were made immediately prior to being used by dissolving 3.803 g of GA with 50.000 g of DI water in a 250 mL beaker.

A 500 mL 0.6M NaOH stock solution was created by diluting 30 mL of the 10N NaOH with DI water in a 500 mL volumetric flask. This stock solution was used as the titrant for both GA solutions.

A 50 mL burette (0.1 mL increments) equipped with a stopcock was used to dispense the NaOH stock solution in various increments directly into the 250 mL beakers containing the ~1M GA solutions. During titration the GA solutions were stirred using a polytetrafluoroethylene coated magnetic stir bar and plate. The volume of NaOH stock dispensed was monitored and recorded through the titrations. The pH of the GA solution was also monitored and recorded with each increment of NaOH stock added. pH measurements were determined through use of a pH meter (VWR Scientific; Model 8000) and electrode (VWR Scientific, P/N 14002-780) calibrated between pH=4.00 and 7.00 using standard buffer solutions (VWR Scientific, P/N 34170-130 and 34170-127, respectively). Titration was carried out until minimal changes of pH in the alkaline range were seen with consecutive additions of the stock solution. Titration curves (pH of GA solution vs. mL 0.6M NaOH) were plotted and comparisons were made to detect effects of gamma irradiation on crystalline GA.

A 300 g batch of an SR material as described in Example 1 (Configuration 1 with NA-GA in solution) was blended for 20 min in a 1 qt acrylic V-shell using a 60 Hz P-K Twin-Shell Yoke blender (Patterson-Kelley Co.; East Stroudsburg, Pa.). All pastes created with Configuration 1 were produced using 0.6M Na-GA solution at a liquid weight to powder weight ratio (L/P) value of 0.23.

Twenty-five (25) 15 cc injectable kits of a modified SR material (Configuration 2 comprising 1.290 wt % of ≤45 μm Na-GA powder) were prepared (35.00 g±0.01 g powder and 7.59 g±0.01 g sterile water for irrigation) from a 1013.071 g batch blended for 20 min in a 2 qt stainless V-shell using a 60 Hz P-K Twin-Shell Yoke blender. The water was overfilled by 0.10 g to account for solution loss in the vial during transfer. The kits were subjected to gamma radiation sterilization (25-32 kGy dosage). Four of these kits were used for this study.

The L/P value for Configuration 2 is 0.214. The difference in L/P values for the two configurations is due to the movement of the Na-GA from the solution to the powder.

Results:

The results of the Vicat set time showed Configuration 2 to have shifted the Vicat set time out by a small amount. Other than the location of the Na-GA within the two configurations, the only other variable is that the Configuration 2 kits were irradiated, while the Configuration 1 materials were not. To address these two variables, Vicat set time of two additional samples for each configuration were taken; however, the Configuration 2 samples were not subjected to sterilization.

Two 35 g units of Configuration 1 powder were tested for Vicat set time. The entire mix was transferred to a 50 mL polystyrene beaker cup (VWR Scientific P/N 13916-015); the paste was leveled and major air pockets were removed through the gentle tapping of the cup on a table. Vicat set time was determined through the same method as performed above on both samples.

Two units of Configuration 2 powder were tested, and the entire mix was used to determine Vicat set times as performed in the previous paragraph. One of the mixes was performed with 30 g of powder due to lack of material.

The new data obtained for Configuration 1 was combined with results from the previous Vicat testing since there was no difference in the treatment of the specimens other than volume. The new data for Configuration 2 was used independently to compare against the Configuration 1 results.

FIG. 5 shows the overlaid curves of the titrations of the 1M GA solutions produced from crystalline GA with and without gamma sterilization. The resulting curves are indistinguishable. As noted in Example 3, solutions of Na-GA used in the manufacturing of Configuration 1 kits displayed a pH shift post gamma radiation sterilization. However, this change in pH was not seen for a solution created with GA gamma irradiated in the crystalline form. This result is indicative that degradation via gamma irradiation of the glycolate ion is greatly, if not completely, alleviated by exposure in the crystalline form. This is strong evidence that the crystalline Na-GA component in Configuration 2 will also be less affected by gamma irradiation.

Table 2 below shows the average results from the 24 hr dry DTS testing of each configuration. Both configurations exhibited DTS values close to 9 MPa with less than a 10% coefficient of variance within each group. Although Configuration 2 exhibited a slightly higher average strength value of 9.29 MPa, the difference between the two configurations was not statistically significant (p=0.25). The observed difference can be attributed to error inherent of the test methodology. These results show that the final set cement of both configurations exhibit the same mechanical strengths.

TABLE 2

| 24 hr DTS (MPa), n = 6 | |
| --- | --- |
| Configuration | Avg. [SD] |
| 1 | 8.80 [0.62] |
| 2 | 9.29 [0.75] |

Table 3 below shows the average results from the four day dissolution test of each configuration. The two configurations exhibited almost identical dissolution results with average weight percent remaining values of 63% after four days. The similarity in the measurements shown for each configuration is further justification of both systems resulting in the same reaction chemistries and extent of reactions.

TABLE 3

| 4 Day Dissolution (wt % remaining), n = 5 | |
| --- | --- |
| Configuration | Avg. [SD] |
| 1 | 63.24 [3.72] |
| 2 | 62.55 [1.94] |

SEM micrographs of typical features seen throughout the bulk of the set cements taken of the fracture surface of a DTS specimen made from each of the configurations were reviewed. The final products of each configuration are substantially identical based on this microscopic evaluation.

Table 4 below shows the average injection force and Vicat set time results for each configuration. Both configurations exhibit very similar injection force results with averages differing by less than 10 N, which is less than 3% of the overall average. The coefficients of variance for both measurements are below 6%, demonstrating good reproducibility in the methodology. The average injection force of Configuration 2, 336.9 N, was slightly (2.6%) lower than that of Configuration 1. These results show equivalence in the viscosities and flow characteristics of pastes made from both configurations.

TABLE 4

Injection Force and Vicat Set Time, n = 3

| Configuration | Avg. Inj. Force (N) [SD] | Avg. Set Time (mm:ss) [SD] |
| --- | --- | --- |
| 1 | 346.0 [19.6] | 15:00 [00:30] |
| 2 | 336.9 [13.4] | 17:40 [01:26] |

The two configurations did exhibit a difference in the Vicat set time measurements. The average Vicat set time for Configuration 2 was 17:40 (mm:ss), which is 2:40 longer than that seen for Configuration 1. With a standard deviation of 30 sec, the Configuration 1 measurements resulted in a very tight data spread in comparison to the Configuration 2 data, the standard deviation of which was 1:26. There is clearly a difference between the Vicat set time of Configuration 1 and gamma sterilized Configuration 2.

In order to address the shift in Vicat set time shift seen for the irradiated Configuration 2 kits, two additional Vicat set time measurements were taken of each configuration. The Configuration 2 powder retained prior to sterilization was used to determine if the shift was induced by the radiation or from the relocation of the Na-GA. Table 5 below shows the average Vicat set time results for the two configurations. Results presented for Configuration 1 are the combined results from the two additional units as well as the three measurements presented above.

TABLE 5

Vicat Set Time for Unsterilized Configurations, n = 5 Config. 1; n = 2 Config. 2

| Configuration | Avg. Set Time (mm:ss) [SD] |
| --- | --- |
| 1 | 14:18 [01:02] |
| 2 | 14:45 [00:21] |

In this scenario, the Vicat set times of each configuration matched up very nicely with the difference between the averages being under 30 s, unlike what was seen above for the irradiated Configuration 2 data. This shows that the reaction kinetics for the two configurations result in very similar Vicat set times, and further demonstrates equivalence between the two configurations. The shift in Vicat set time seen in the data presented earlier was the result of gamma irradiation and not differences between the two configurations.

The observation that gamma irradiation induces a shift of Vicat set for Configuration 2 was not unexpected. This observation is consistent with Example 3, where a Configuration 1 type blend of powder showed an increasing average Vicat set time with consecutive doses of gamma irradiation of the Na-GA solution, in the same dose range.

Conclusion:

No statistically significant differences between DTS, dissolution, and injection force values were observed between the two product configurations. A statistical difference in the Vicat set time values was observed when the irradiated Configuration 2 data was evaluated (p-value=0.04), but no difference was seen when the analysis was performed with the unsterilized Configuration 2 data (p-value=0.59). This difference can not be blamed on the configuration changes as the second Vicat set time comparison would have resulted in a significant difference as well if relocation of the Na-GA was the cause. Thus, this study shows chemical, physical, mechanical, and morphological equivalence between the two configurations in both the paste and set cement forms.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A particulate composition adapted for forming a bone graft substitute cement upon mixing with an aqueous solution, comprising:
    i) an α-calcium sulfate hemihydrate powder wherein the calcium sulfate hemihydrate is present at a concentration of about 50 weight percent to about 90 weight percent based on the total weight of the particulate composition; and
    ii) a combination of two calcium phosphate powders capable of reacting to form brushite in the presence of an aqueous solution, wherein the combination of two calcium phosphate powders comprises monocalcium phosphate monohydrate powder and β-tricalcium phosphate powder.

2. The particulate composition of claim 1, wherein the β-tricalcium phosphate powder has a median particle size of less than about 20 microns.

3. The particulate composition of claim 2, wherein the β-tricalcium phosphate powder has a median particle size of less than about 18 microns.

4. The particulate composition of claim 3, wherein the β-tricalcium phosphate powder has a median particle size of less than about 15 microns.

5. The particulate composition of claim 1, wherein the β-tricalcium phosphate powder has a bimodal particle size distribution comprising about 30 to about 70 volume percent of particles having a mode of about 2.0 to about 6.0 microns and about 30 to about 70 volume percent of particles having a mode of about 40 to about 70 microns based on the total volume of the β-tricalcium phosphate powder.

6. The particulate composition of claim 5, wherein the β-tricalcium phosphate powder has a bimodal particle size distribution comprising about 50 to about 65 volume percent of particles having a mode of about 4.0 to about 5.5 microns and about 35 to about 50 volume percent of particles having a mode of about 60 to about 70 microns based on the total volume of the β-tricalcium phosphate powder.

7. The particulate composition of claim 1, wherein the monocalcium phosphate monohydrate powder and the β-tricalcium phosphate powder are present in approximately equimolar amounts.

8. The particulate composition of claim 1, wherein the monocalcium phosphate monohydrate powder is present at a concentration of about 3 to about 7 weight percent and the β-tricalcium phosphate powder is present at a concentration of about 3.72 to about 8.67 weight percent, based on the total weight of the particulate composition.

9. The particulate composition of claim 1, wherein the combination of two calcium phosphate powders are present at a concentration of about 3 to about 30 weight percent based on the total weight percent of the particulate composition.

10. The particulate composition of claim 9, wherein the combination of two calcium phosphate powders are present at a concentration of about 10 to about 20 weight percent based on the total weight percent of the particulate composition.

11. The particulate composition of claim 1, wherein the median particle size of the a-calcium sulfate hemihydrate powder is about 5 to about 20 microns.

12. The particulate composition of claim 11, wherein the median particle size of the α-calcium sulfate hemihydrate powder is about 8 to about 15 microns.

13. The particulate composition of claim 12, wherein the median particle size of the α-calcium sulfate hemihydrate powder is about 10 to about 15 microns.

14. The particulate composition of claim 1, wherein the α-calcium sulfate hemihydrate powder has a bimodal particle distribution comprising about 30 to about 60 volume percent of particles having a mode of about 1.0 to about 3.0 microns and about 40 to about 70 volume percent of particles having a mode of about 20 to about 30 microns, based on the total volume of the α-calcium sulfate hemihydrate powder.

15. The particulate composition of claim 14, wherein the α-calcium sulfate hemihydrate powder has a bimodal particle distribution comprising about 40 to about 60 volume percent of particles having a mode of about 1.0 to about 2.0 microns and about 40 to about 60 volume percent of particles having a mode of about 20 to about 25 microns, based on the total volume of the α-calcium sulfate hemihydrate powder.

16. The particulate composition of claim 1, wherein the α-calcium sulfate hemihydrate powder is present at a concentration of at least about 70 weight percent to about 90 weight percent based on the total weight of the particulate composition.

17. The particulate composition of claim 16, wherein the α-calcium sulfate hemihydrate powder is present at a concentration of at least about 75 weight percent to about 90 weight percent based on the total weight of the particulate composition.

18. The particulate composition of claim 1, further comprising a plurality of β-tricalcium phosphate granules.

19. The particulate composition of claim 18, wherein the β-tricalcium phosphate granules have a median particle size of at least about 75 microns.

20. The particulate composition of claim 19, wherein the β-tricalcium phosphate granules have a median particle size of about 75 to about 1,000 microns.

21. The particulate composition of claim 20, wherein the β-tricalcium phosphate granules have a median particle size of about 100 to about 400 microns.

22. The particulate composition of claim 21, wherein the β-tricalcium phosphate granules have a median particle size of about 180 to about 240 microns.

23. The particulate composition of claim 18, wherein the β-tricalcium phosphate granules are present at a concentration of up to about 20 weight percent based on the total weight of the particulate composition.

24. The particulate composition of claim 23, wherein the β-tricalcium phosphate granules are present at a concentration of up to about 15 weight percent based on the total weight of the particulate composition.

25. The particulate composition of claim 24, wherein the β-tricalcium phosphate granules are present at a concentration of up to about 12 weight percent based on the total weight of the particulate composition.

26. The particulate composition of claim 25, wherein the β-tricalcium phosphate granules are present at a concentration of about 8 to about 12 weight percent based on the total weight of the particulate composition.

27. The particulate composition of claim 1, further comprising an accelerant adapted for accelerating the conversion of calcium sulfate hemihydrate to calcium sulfate dihydrate.

28. The particulate composition of claim 27, wherein the accelerant is selected from the group consisting of calcium sulfate dihydrate particles, potassium sulfate particles, and sodium sulfate particles, wherein the accelerant is optionally coated with sucrose.

29. The particulate composition of claim 27, wherein the accelerant is present at a concentration of up to about 1 weight percent based on the total weight of the particulate composition.

30. The particulate composition of claim 1, further comprising a biologically active agent.

31. The particulate composition of claim 30, wherein the biologically active agent is an osteoinductive material.

32. The particulate composition of claim 31, wherein the osteoinductive material is demineralized bone matrix.

33. The particulate composition of claim 30, wherein the biologically active agent is a growth factor.

34. The particulate composition of claim 1, wherein the particulate composition sets to a hardened mass upon mixing with an aqueous solution in about 3 to about 25 minutes.

35. The particulate composition of claim 34, wherein the particulate composition sets to a hardened mass upon mixing with an aqueous solution in about 10 to about 20 minutes.

36. The particulate composition of claim 1, wherein all of the powder components of the particulate composition are in admixture.

37. The particulate composition of claim 1, wherein the powder components of the particulate composition are in one or more containers.

38. The particulate composition of claim 1, wherein the particulate composition further comprises a plurality of β-tricalcium phosphate granules having a median particle size greater than the particle size of the β-tricalcium phosphate powder.

39. The particulate composition of claim 1, wherein the particulate composition further comprises demineralized bone matrix.

40. A bone graft substitute cement comprising the reaction product formed by mixing a particulate composition according to claim 1 with an aqueous solution, the reaction product comprising calcium sulfate dihydrate and brushite.

41. The bone graft substitute cement of claim 40, wherein said cement exhibits a diametral tensile strength of at least about 6 MPa after curing for one hour in ambient air following mixing of the particulate composition with the aqueous solution.

42. The bone graft substitute cement of claim 40, wherein said cement exhibits a diametral tensile strength of at least about 10 MPa after curing for 24 hours in ambient air following mixing of the particulate composition with the aqueous solution.

43. The bone graft substitute cement of claim 40, wherein said cement exhibits a compressive strength of at least about 40 MPa after curing for one hour in ambient air following mixing of the particulate composition with the aqueous solution.

44. The bone graft substitute cement of claim 40, wherein said cement exhibits a compressive strength of at least about 80 MPa after curing for 24 hours in ambient air following mixing of the particulate composition with the aqueous solution.

45. The bone graft substitute cement of claim 40, wherein the aqueous solution comprises a carboxylic acid.

46. The bone graft substitute cement of claim 45, wherein the carboxylic acid is a hydroxy carboxylic acid.

47. The bone graft substitute cement of claim 46, wherein the hydroxy carboxylic acid is glycolic acid.

48. The bone graft substitute cement of claim 45, wherein the carboxylic acid is neutralized to a pH of about 6.5 to about 7.5.

49. The bone graft substitute cement of claim 40, wherein the aqueous solution is mixed with the particulate composition in an amount necessary to achieve a liquid to powder mass ratio of at least about 0.2.

50. The bone graft substitute cement of claim 40, wherein the bone graft substitute cement is injectable prior to setting into a hardened form.

51. A bone graft substitute kit, comprising one or more containers enclosing a radiation-sterilized particulate composition according to claim 1, and a separate container enclosing a radiation-sterilized aqueous solution.

52. The bone graft substitute kit of claim 51, further comprising one or more of the following:
    a written instruction set describing a method of using said kit;
    a mixing apparatus adapted for mixing the particulate composition and the aqueous solution; and
    a delivery device adapted for delivering a bone graft substitute cement mixture to the site of a bone defect.

53. A method for treating a bone defect, comprising applying a bone graft substitute cement according to claim 40 to the site of the bone defect.

54. A method for preparing an orthopedic implant for implantation, comprising applying a bone graft substitute cement according to claim 40 to the orthopedic implant.

55. The method of claim 54, wherein the orthopedic implant is a joint replacement device.

56. The method of claim 55, wherein the joint replacement device is selected from the group consisting of knee replacement devices, hip replacement devices, elbow replacement devices, upper femoral devices, upper humeral devices, wrist replacement devices, shoulder devices, passive tendon devices, spinal devices, finger/toe devices, and diaphysis devices.

57. A bone graft substitute cement comprising a mixture of a calcium sulfate dihydrate phase characterized by a first in vivo resorption rate, a brushite phase characterized by a second in vivo resorption rate slower than the first in vivo resorption rate; and a β-tricalcium phosphate granule phase characterized by a third in vivo resorption rate slower than the second in vivo resorption rate, wherein the cement is formed by mixing a particulate composition with an aqueous solution, wherein the particulate composition includes an α-calcium sulfate hemihydrate powder, and a combination of two calcium phosphate powders, wherein the combination of two calcium phosphate powders comprises monocalcium phosphate monohydrate powder and β-tricalcium phosphate powder, and wherein the α-calcium sulfate hemihydrate is present at a concentration of about 50 weight percent to about 90 weight percent based on the total weight of the particulate composition.

58. The bone graft substitute cement of claim 57, wherein the bone graft substitute cement is injectable prior to setting into a hardened form.

59. A bone graft substitute kit, comprising:
    a sterilized particulate composition adapted for forming a bone graft substitute cement upon mixing with an aqueous solution, wherein the particulate composition comprises i) an α-calcium sulfate hemihydrate powder, wherein the calcium sulfate hemihydrate is present at a concentration of about 50 weight percent to about 90 weight percent based on the total weight of the particulate composition; and ii) a combination of two calcium phosphate powders capable of reacting to form brushite in the presence of an aqueous solution, wherein the combination of two calcium phosphate powders comprises monocalcium phosphate monohydrate powder and β-tricalcium phosphate powder, wherein the two calcium phosphate powders are stored separate from each other in the kit; and
    a sterilized aqueous solution comprising a carboxylic acid dissolved therein stored separately from the particulate composition in the kit.

60. The bone graft substitute kit of claim 59, wherein the aqueous solution and the particulate composition are both radiation sterilized.

61. The bone graft substitute kit of claim 59, further comprising one or more of the following:
    a written instruction set describing a method of using said kit;
    a mixing apparatus adapted for mixing the particulate composition and the aqueous solution; and
    a delivery device adapted for delivering a bone graft substitute cement mixture to the site of a bone defect.

62. A method for treating a bone defect, comprising:
    mixing a particulate composition with an aqueous solution to form a bone graft substitute cement, wherein the particulate composition comprises an α-calcium sulfate hemihydrate powder and a combination of two calcium phosphate powders capable of reacting to form brushite in the presence of an aqueous solution, wherein the combination of two calcium phosphate powders comprises monocalcium phosphate monohydrate powder and β-tricalcium phosphate powder wherein the calcium sulfate hemihydrate is present at a concentration of about 50 weight percent to about 90 weight percent based on the total weight of the particulate composition; and
    applying the bone graft substitute cement to the bone defect.

63. The method of claim 62, wherein the applying step comprises injecting the bone graft substitute cement into the bone defect.

64. The method of claim 62, wherein the bone graft substitute cement comprises a mixture of a calcium sulfate dihydrate phase characterized by a first in vivo resorption rate and a brushite phase characterized by a second in vivo resorption rate slower than the first in vivo resorption rate.

65. The method of claim 64, wherein the particulate composition further comprises a plurality of β-tricalcium phosphate granules such that the β-tricalcium phosphate granules provide a third in vivo resorption rate slower than the second in vivo resorption rate.

66. The method of claim 62, wherein the particulate composition further comprises a plurality β-tricalcium phosphate granules having a median particle size greater than the particle size of the β-tricalcium phosphate powder.

67. The method of claim 62, wherein the particulate composition further comprises demineralized bone matrix.

68. The method of claim 62, wherein the aqueous solution is mixed with the particulate composition in an amount necessary to achieve a liquid to powder mass ratio of at least about 0.2.

69. The method of claim 62, wherein the cement exhibits a diametral tensile strength of at least about 6 MPa after curing for one hour in ambient air following mixing of the particulate composition with the aqueous solution.

70. The method of claim 62, wherein the cement exhibits a diametral tensile strength of at least about 10 MPa after curing for 24 hours in ambient air following mixing of the particulate composition with the aqueous solution.

71. The method of claim 62, wherein the cement exhibits a compressive strength of at least about 40 MPa after curing for one hour in ambient air following mixing of the particulate composition with the aqueous solution.

72. The method of claim 62, wherein the cement exhibits a compressive strength of at least about 80 MPa after curing for 24 hours in ambient air following mixing of the particulate composition with the aqueous solution.

73. The method of claim 62, wherein the aqueous solution comprises a carboxylic acid.

74. The method of claim 73, wherein the carboxylic acid is a hydroxy carboxylic acid.

75. The method of claim 74, wherein the hydroxy carboxylic acid is glycolic acid.

76. The method of claim 73, wherein the carboxylic acid is neutralized to a pH of about 6.5 to about 7.5.

77. The method of claim 62, wherein application of the bone graft substitute cement results in new bone formation at the site of the bone defect characterized by a yield strength greater than normal bone at 13 weeks after application of the bone graft substitute cement.

* * * * *